US012357250B2

(12) United States Patent
Perrin et al.

(10) Patent No.: US 12,357,250 B2
(45) Date of Patent: Jul. 15, 2025

(54) SYSTEM AND METHOD OF USING TEMPORAL MEASUREMENTS OF LOCALIZED RADIATION TO ESTIMATE THE MAGNITUDE, LOCATION, AND VOLUME OF RADIOACTIVE MATERIAL IN THE BODY

(71) Applicant: Lucerno Dynamics, LLC, Cary, NC (US)

(72) Inventors: Steven Perrin, Durham, NC (US); Joshua G. Knowland, Cary, NC (US)

(73) Assignee: Lucerno Dynamics, LLC, Cary, NC (US)

( * ) Notice: Subject to any disclaimer, the term of this patent is extended or adjusted under 35 U.S.C. 154(b) by 748 days.

(21) Appl. No.: 16/837,187

(22) Filed: Apr. 1, 2020

(65) Prior Publication Data

US 2020/0315558 A1 Oct. 8, 2020

Related U.S. Application Data

(60) Provisional application No. 62/828,033, filed on Apr. 2, 2019.

(51) Int. Cl.
*A61B 6/40* (2024.01)
*A61B 6/42* (2024.01)
*G01T 1/164* (2006.01)

(52) U.S. Cl.
CPC .......... *A61B 6/4057* (2013.01); *A61B 6/4258* (2013.01); *A61B 6/4266* (2013.01); *G01T 1/1641* (2013.01)

(58) Field of Classification Search
CPC ..... A61B 6/037; A61B 6/4057; A61B 6/4258; A61B 6/4266; A61B 6/486; A61B 6/504; G01T 1/1641; G01T 7/005
See application file for complete search history.

(56) References Cited

U.S. PATENT DOCUMENTS 4,095,107 A * 6/1978 Genna ................... A61B 6/037
250/363.04
4,629,894 A 12/1986 Lelong
(Continued)

FOREIGN PATENT DOCUMENTS

JP 2002196080 A 7/2002
JP 2009133803 6/2009
(Continued)

OTHER PUBLICATIONS

International Search report dated Feb. 19, 2014.
(Continued)

*Primary Examiner* — Ashley K Buran
*Assistant Examiner* — Maria Christina Talty
(74) *Attorney, Agent, or Firm* — Williams Mullen; Andrew R. Shores

(57) ABSTRACT

A system and method for the measurement of radiation emitted from the body, for example, is presented. In one example, radiation sensors (e.g., gamma radiation sensors) may be used to measure activity proximate an injection site as a function of time. With that data, a function describing an amount of radioactive material in tissue proximate the injection site as a function of time may be estimated where an amount of radioactive material in the tissue at a time t is known. When an array of sensors is employed, the amount of radioactive material in the tissue proximate the injection site may be determined directly by the system. With an estimated function of radioactive material proximate the injection site as a function of time known, an estimated arterial input function may be determined, allowing for calculation of a correction factor that may be applied by a clinician during nuclear medical imaging.

16 Claims, 17 Drawing Sheets

(56) References Cited

U.S. PATENT DOCUMENTS

| | | | |
|---|---|---|---|
| 4,682,604 | A | 7/1987 | Fymat et al. |
| 4,692,890 | A | 9/1987 | Arseneau |
| 4,881,171 | A | 11/1989 | Jattteau et al. |
| 5,007,427 | A | 4/1991 | Suzuki et al. |
| 5,309,357 | A | 5/1994 | Stark et al. |
| 5,428,223 | A | 6/1995 | Jatteau et al. |
| 5,583,343 | A | 12/1996 | Dilmania et al. |
| 5,647,363 | A | 7/1997 | Rabito et al. |
| 5,821,538 | A | 10/1998 | De Antoni et al. |
| 6,448,544 | B1 | 9/2002 | Stanton et al. |
| 7,711,409 | B2 | 5/2010 | Keppel et al. |
| 7,972,259 | B2 * | 7/2011 | Rozenfeld ............ A61N 5/1048 600/3 |
| 8,565,860 | B2 | 10/2013 | Kimchy et al. |
| 8,680,476 | B2 | 3/2014 | Webster et al. |
| 9,939,533 | B2 * | 4/2018 | Knowland ............ A61B 6/463 |
| 10,471,162 | B2 * | 11/2019 | Desogere ............ A61K 51/08 |
| 2001/0002250 | A1 * | 5/2001 | Burbank ............ A61B 10/0266 424/9.1 |
| 2002/0137991 | A1 | 9/2002 | Scarantino et al. |
| 2003/0012731 | A1 | 1/2003 | Suddarth et al. |
| 2003/0108229 | A1 * | 6/2003 | Tanaka ............ A61B 6/037 382/131 |
| 2003/0189657 | A1 | 10/2003 | Hammadou |
| 2005/0143927 | A1 | 6/2005 | Cammia et al. |
| 2005/0287065 | A1 | 12/2005 | Suddarth et al. |
| 2006/0076523 | A1 | 4/2006 | Higashiisogawa et al. |
| 2008/0161632 | A1 * | 7/2008 | Rozenfeld ............ A61N 5/1027 600/1 |
| 2009/0150315 | A1 | 6/2009 | Wirtz et al. |
| 2009/0226915 | A1 | 9/2009 | Guyon |
| 2009/0250602 | A1 | 10/2009 | Black et al. |
| 2009/0266993 | A1 | 10/2009 | Baerwolff et al. |
| 2010/0010343 | A1 | 1/2010 | Daghighian et al. |
| 2010/0198061 | A9 | 8/2010 | Daghighian et al. |
| 2010/0268078 | A1 | 10/2010 | Suddarth et al. |
| 2011/0196234 | A1 | 8/2011 | Buono et al. |
| 2011/0301863 | A1 | 12/2011 | Auribault et al. |
| 2014/0018675 | A1 | 1/2014 | Keppel et al. |
| 2015/0276937 | A1 * | 10/2015 | Knowland ............ G01T 1/161 600/431 |
| 2016/0303397 | A1 | 10/2016 | Hirschman et al. |
| 2017/0360967 | A1 * | 12/2017 | Desogere ............ A61K 51/08 |
| 2018/0047555 | A1 | 2/2018 | Pringle et al. |
| 2018/0172844 | A1 | 6/2018 | Knowland et al. |
| 2020/0031558 | A1 | 1/2020 | Iwamoto |
| 2021/0015434 | A1 | 1/2021 | Perrin et al. |
| 2021/0128082 | A1 | 5/2021 | Cohen et al. |

FOREIGN PATENT DOCUMENTS

| | | |
|---|---|---|
| JP | 2011163966 A | 5/2011 |
| JP | 2016197092 | 11/2016 |
| WO | 2007140352 A2 | 12/2007 |
| WO | 2009158143 A1 | 12/2009 |
| WO | 2010039298 A2 | 4/2010 |
| WO | 2020206092 | 10/2020 |

OTHER PUBLICATIONS

Son, C. et al, An Implantable Wireless Microdosimeter for Radiation Oncology, School of Electrical and Computer Engineering, Mems 2008, Jan. 13-17, 2008, pp. 256-259.

Basak, Abhishek, Low-Power Implantable Ultrasound Imager for Online Monitoring of Tumor Growth, 33rd Annual Intl Conference of the IEEE EMBS, Boston, MA., Aug. 30-Sep. 3, 2011, pp. 2858-2861.

Extended European Search Report dated Nov. 11, 2016.

S.D. Wollenweber et al, "A Simple On-Line Arterial Time-Activity Curve Detector for [0-15] Water PET Studies", IEEE Transactions on Nuclear Science, vol. 44, No. 3, pp. 1417-1419, Jun. 1997.

Weber, A. Wolfgang, Use of PET for Monitoring Cancer Therapy and for Predicting Outcome, The Journal of Nuclear Medicine, vol. 46, No. 6, Jun. 2005 pp. 983-995.

Delbeke, Dominique et al., Procedure Guideline for Tumor Imaging with 18F-FDG PET/CT 1.0, The Journal of Nuclear Medicine, vol. 47, No. 5, May 2006 pp. 885-895.

Dunnwald, Lisa et al., PET Tumor Metabolism in Locally Advanced Breast Cancer Patients Undergoing Neoadjuvant Chemotherapy: Value of Static versus Kinetic Measures of Fluorodeoxyglucose Uptake, Clinical Cancer Research, vol. 17, No. 8, Apr. 15, 2011, pp. 2400-2409.

Velasquez, Linda M. et al., Repeatability of 18F-FDG PET in a Multicenter Phase I Study of Patients with Advanced Gastrointestinal malignancies, The Journal of Nuclear Medicine, vol. 50, No. 10, Oct. 2009, pp. 1646-1654.

Osman, Medhat M. et al., FDG dose extravasations in PET/CT: frequency and impact on SUV measurements, Front. Oncol., Nov. 16, 2011, http://journal.frontiersin.org/article/10.3389/fonc.2011.00041/full.

Office Action dated Aug. 15, 2014.

European Patent Office, Search Report for International Patent Application No. 20784501.7, Nov. 7, 2022.

United States Patent and Trademark Office (USPTO), Non-Final Office Action for U.S. Appl. No. 17/062,133, filed May 4, 2023.

Japan Patent Office, Office Action for International Patent Application No. JP 2021-560415, Jan. 22, 2024.

Japanese Patent Office, Japanese Examination Report for International Patent Application No. JP2021-560415, Jun. 24, 2024.

United States Patent and Trademark Office, Office Action for U.S. Appl. No. 17/062,133, filed Oct. 24, 2024.

Australia Patent and Trademark Office, Australian Examination Report for International Patent Application No. AU2020256211, Oct. 9, 2024.

* cited by examiner

SYSTEM AND METHOD OF USING TEMPORAL MEASUREMENTS OF LOCALIZED RADIATION TO ESTIMATE THE MAGNITUDE, LOCATION, AND VOLUME OF RADIOACTIVE MATERIAL IN THE BODY

PRIORITY

This application claims priority to U.S. Provisional Patent Application No. 62/828,033, filed Apr. 2, 2019, the entirety of which is incorporated herein by reference.

FIELD OF THE INVENTION

The present invention relates to systems, devices, and methods of measuring and quantifying the magnitude, location, and/or volume of radioactive material in the body. More particularly, the present disclosure teaches novel systems, devices and methods of determining and/or quantifying the amount of radioactive material in an area of interest in the body, whether the radioactive material be introduced via an infiltrated injection, uptake in a tumor, uptake in an organ, or any other introduction of radioactive material to all or part of the body, or radioactive material anywhere generally.

BACKGROUND

Numerous medical diagnostics and therapies today involve the introduction of radiopharmaceuticals into the body, whether it be to enhance nuclear imaging techniques, attack tumors, or other purposes. Oncologists, for example, may be interested in knowing if a prescribed cancer therapy is having an intended effect, in order to improve outcomes, minimize side effects, and avoid unnecessary expenses. Cytotoxic treatments, for example, kill tumor cells. Cytostatic treatments, for example, inhibit cell growth leaving tumors the same size, but preventing the spread of the disease. As another example, immunotherapy treatments use the body's immune system to attack the cancer and initially result in an inflammatory response in the tumor area before there is evidence that the body is effectively attacking the tumor. Historically, measuring the size of the tumor has been a primary way for oncologists to assess treatment effectiveness; however, we now understand that the physical size of the tumor is often not the best or earliest indicator of the therapy effectiveness. For example, with cytotoxic treatment the tumor size reduction only occurs after cancer cells die and the body's natural processes eliminate dead cells; this process can often take weeks. With cytostatic treatment, cancer cells stop growing leaving the clinician unsure of the state of the underlying cancer. With immunotherapy, the body's inflammatory response often masks the tumor from proper evaluation. These are just some of the many challenges facing clinicians today.

The tools presently available to oncologists and researchers to assess tumor response to treatments are not ideal. Palpating the tumor is easy and inexpensive, but it is limited to tumors close to the surface, relies on a physician's memory and notes, and primarily measures size. The lack of reproducibility of this palpating process, coupled with historical reasons, contributed to the initial acceptance of significant changes in tumor size as an indicator of therapy assessment. Wolfgang A. Weber, et al., "Use of PET for Monitoring Cancer Therapy and for Predicting Outcome," 46 J. Nucl. Med. (No. 6) 983-995 (June 2005). Imaging tools (CT, MRI, x-ray) provide more precise measurements for tumors both close to the surface and in deep tissue, but again primarily measure size, not the ideal indicator. Molecular imaging (single-photon emission computerized tomography (SPECT) or PET/CT scan, for example) may capture the gamma particle emissions from injected radio-labeled tracers captured by live cancer cells and is routinely used for pre-therapy staging of cancer. Visually identifying metastatic disease is the primary means of staging cancer; however, semi-quantitative measurements, for example the Standardized Uptake Value (SUV), may also be used to stage cancer and other conditions. For example, semi-quantitative measurements may be used to help determine whether lung nodules are malignant, or brain function is deteriorating. In general, semi-quantitative measurements may include a ratio of the amount of radio-labeled tracer in an area of interest (e.g., a tumor) compared to the level in a reference area, for example the rest of the body. For example, while molecular imaging is a primary tool for the pre-therapy need to stage a patient's cancer, it is also rapidly becoming the most advanced tool for oncologists and researchers to assess tumor response, since molecular imaging can capture the metabolic or proliferative condition of the cancer and/or the size of the tumor. Using measurements taken from the staging metabolic imaging scans and then comparing these values to a follow-up imaging scan is currently one of the best available indicators for therapy effectiveness.

SPECT imaging using I-Ioflupane (DaTSCAN or [123I] FP-CIT) is another sensitive imaging technique. In some clinical and/or research settings, SPECT imaging may be used to detect or classify certain diseases, including diseases of the brain such as Parkinsonian Syndromes. By way of just one example, it may be desirable to distinguish certain neurodegenerative Parkinsonian Syndromes from other non-degenerative Parkinsonian Syndromes and other tremor disorders. By measuring uptake of a radiotracer in certain areas of the brain, SPECT images may be used to make such distinctions. For example, scans may be characterized by intense and symmetric DAT binding in the caudate nucleus and putamen on both hemispheres of the brain, as opposed to asymmetric measurements that may indicate degenerative conditions. See, e.g., R. Prashanth, S. Dutta Roy, P. Mandal, and S. Ghosh, "High Accuracy Classification of Parkinson's Disease through Shape Analysis and Surface Fitting in $^{123}$-Ioflupane SPECT Imaging," IEEE-JBHI Journal (2016). Quantifying these measurements in one or more locations, or otherwise enabling a comparison between regions of the body or organ (e.g., comparisons between halves of the brain) may provide helpful diagnostic or other information (e.g., estimations of the Striatal Binding Ratio (SBR)). It may be possible, for example, to use such information to diagnose degenerative brain conditions using such techniques (and/or eliminate such diagnoses).

Despite the increasing trend to use comparative molecular imaging scans in assessing response in more and more conditions as clinical evidence continues to grow, there are still limitations with this assessment tool. For example, molecular imaging scans are expensive, and their use is often challenged based on cost. Additionally, there are several issues with semi-quantitative measurements such as SUV. According to Dr. Dominique Delbeke: "[t]he reproducibility of SUV measurements depends on the reproducibility of clinical protocols, for example, dose infiltration, time of imaging after 18F-FDG administration, type of reconstruction algorithms, type of attenuation maps, size of the region of interest, changes in uptake by organs other than the tumor, and methods of analysis (e.g., maximum and mean)." Dominique Delbeke, et al., "Procedure Guideline for Tumor Imaging with 18F-FDG PET/CT 1.0," 47 J. Nucl. Med. (No. 5) 885-895 (May 2006). Infiltrated injection (extravasation) of radio-labeled tracer is an exemplary complication that often goes unnoticed by clinicians. Medhat Osman, "FDG Dose Extravasations in PET/CT: Frequency and Impact on SUV Measurements," Frontiers in Oncology (Vol. 1:41) 1 (2011). An infiltration is a common problem that can occur when the radio-labeled tracer infuses the tissue near the venipuncture site and can result from the tip of the catheter slipping out of the vein or passing through the vein. Additionally, the blood vessel wall can allow part of the tracer to infuse the surrounding tissue. As a result, the radio-labeled dose being delivered is inaccurate and thus so are the SUV calculations, which can severely impact patient treatment and research conclusions. These infiltrations may in fact contribute to the wide variability in researchers' efforts to characterize SUV thresholds for clinical decision making. In one study, it was determined that the "thresholds for metabolic response in the multicenter multiobserver non-QA settings were −34% and 52% and in the range of −26% to 39% with centralized QA". Linda M. Velasquez, et al., "Repeatability of 18F-FDG PET in a Multicenter Phase I Study of Patients with Advanced Gastrointestinal Malignancies," 50 J. Nucl. Med. (No. 10) 1646-1654 (October 2009). In local practices and even in practices and research centers employing Quality Assurance checks, these issues with SUV calculations have left oncologists and researchers needing to see significant changes in SUV values to be somewhat assured they are making sound treatment decisions or reaching proper research conclusions.

While using SUVs comparisons from static images is currently the most advanced way in clinical practice to assess tumor response to treatment, the use of dynamic molecular images (i.e., images taken at various times during the uptake of the radio-labeled tracers) has provided researchers with kinetic information regarding the uptake of radio-labeled tracers. In the academic community, this kinetic information is proving to be an even better method of assessing treatment and predicting patient outcomes than using static semi-quantitative measurements such as SUV. (See Lisa K. Dunnwald, "PET Tumor Metabolism in Locally Advanced Breast Cancer Patients Undergoing Neoadjuvant Chemotherapy: Value of Static versus Kinetic Measures of Fluorodeoxyglucose Uptake," Clin. Cancer Res. 2011;17:2400-2409 (published online first Mar. 1, 2011)). Unfortunately, this dynamic approach takes approximately three times as long as a static scan and thus would require several more scanners at each hospital; it is clinically and economically impractical for widespread adoption and clinical use. So while there have been great improvements in the past few decades regarding cancer treatment options, today's clinicians and researchers continue to lack a timely, cost-effective, and fast way to evaluate the effectiveness of the treatments they deliver or the research they are conducting.

In light of the problems associated with current measurement and prediction systems, systems and methods for identifying improperly administered radio-labeled tracer injections (infiltrations or extravasation), which negatively impact tissue uptake and SUV results, and easier, less costly, and more efficient systems and methods for measuring and predicting the status and/or changes in such biological processes have also been developed. For example, methods and systems for detection of radioactive materials in the body over a desired period of time have are disclosed in, for example, U.S. application Ser. No. 15/885,112 filed Jan. 31, 2018, which is a divisional of U.S. application Ser. No. 14/678,550 filed on Apr. 3, 2015, now U.S. Pat. No. 9,939,533, which is a continuation-in-part of U.S. application Ser. No. 13/840,925 filed on Mar. 15, 2013, now U.S. Pat. No. 9,002,438, which claims the benefit of priority to U.S. Provisional Application No. 61/653,014, filed on May 30, 2012. Each of these disclosures are incorporated fully herein by reference.

Certain aspects of the systems and methods disclosed in the references identified above relate to, among other things, the detection and quantification of infiltrations during injections of radio-labeled radiotracers (i.e., non-bolus injections). In nuclear medicine procedures, radiopharmaceuticals are typically injected intravenously. For many of these procedures, the injection should be administered as a bolus that results in complete and prompt systemic distribution of the radiopharmaceutical. An extravasation, or infiltration, occurs when an injected substance leaks into surrounding tissue instead of remaining within the vasculature as intended. Extravasations can be caused by improper placement of the intravenous access (IV), erosion or degradation of the vessel wall, or failure of vessel integrity. When any radiopharmaceutical is extravasated, some of the activity remains at the injection site instead of circulating throughout the patient's body. Extravasations reduce the net available activity for uptake and alter the uptake kinetics for subsequent imaging. Extravasations may also undesirably expose tissue surrounding the extravasation to unacceptable doses of radiation.

While the general detection alone of infiltrations or non-bolus injections is extremely useful to clinicians, it would be advantageous to have an understanding of not only the fact that an infiltration has occurred, but also how the infiltration may have affected, for example, the total amount of radiotracer that ultimately reaches the bloodstream, the timing of that delivery to the bloodstream, and ultimately how the measured SUV, for example, in an area of interest may need to be adjusted based on such reduced and/or delayed delivery of radiotracer to the bloodstream. It may also be advantageous to quantify a radiation dose to tissue near the infiltration site.

In particular, in the event of an infiltrated injection, a portion of the radio-tracer may go directly to the bloodstream while a portion remains embedded in tissue around the injection site. The radio-tracer embedded in the tissue may still ultimately reach the bloodstream, albeit at a time later than the initial injection, thereby affecting certain assumptions in dosage and delivery made by the clinicians. Accordingly, because non-bolus injections may alter the metrics measured by, for example, a PET scan dynamically over a period of time (e.g., kinetic analysis, Patlak, etc.), and because the dynamic variation depends on the nature of the infiltration itself (i.e., varies from infiltration to infiltration), a system and method for measuring the delivery of radio-tracer from an infiltrated injection to the bloodstream as a function of time may provide critical information to clinicians.

It is therefore one object of the present disclosure to provide methods and systems for estimating the initial magnitude of an infiltrated injection, and to measure the rate of delivery of some or all of the infiltrated portion to the bloodstream over a critical time period. For example, in some embodiments, the systems and methods provided herein may be utilized to ultimately provide a correction factor that may be applied to a measured SUV, among other things.

Further, radiopharmaceutical extravasations can result in high activity remaining near the injection site that exposes the tissue to significant dose. Existing dosimetry techniques may not be suitable for extravasations because they do not accurately account for changes in extravasated activity or volume over time. As explained in some exemplary embodiments herein, scintillation detectors that record time-activity curves (TACs) of the activity near the injection site may be a practical way to gather this information. For example, the rate of biological clearance of the extravasate may be determined with TAC data. Using this rate, along with the total extravasated activity that may be determined using, for example, nuclear imaging or direct measurement of the magnitude, location, and/or volume of the infiltration at a given point in time, initial extravasation activity may be estimated by extrapolating back to the time of injection.

One aspect of the methods and systems described is to have an understanding of the magnitude/amplitude, location, and/or volume of, for example, an infiltrated portion of a radio-tracer injection as a function of time. Presently, such information may be determined by using, for example, nuclear medicine imaging techniques (e.g., PET scan). However, there are many circumstances where it may be advantageous to determine this information without relying on the nuclear medicine image or scanner itself. For example, the radioactive source of interest may be outside the imaging device's field of view, or may not be able to be determined until after the radioactive source has dissipated or moved, etc. It may also be advantageous to determine this information without relying on an expensive nuclear imaging system (e.g., PET scan, etc.). For example, such systems, devices and methods may be used to quantify and otherwise understand the uptake of radioactive material in a tumor over time, precise organ dosimetry of radiopharmaceuticals, uptake of radiopharmaceuticals in other areas of interest in the body (e.g., brain (basil ganglia), other organs, other tissues, etc.), and other circumstances.

It is therefore an additional object of the present disclosure to provide a method and system of measuring or estimating the amplitude, location, and/or volume of a radioactive source in the body without relying on a nuclear medicine imaging device like a PET scanner and the like. Instead of using the nuclear medicine imaging device (e.g., SPECT or PET scanner) itself to make the necessary measurements, one or more sensors may be used to measure, for example, radiation activity over a period of time. For example, sensors such as those taught in U.S. Pat. Nos. 9,002,438 and 9,939,533 may be used, though other sensors for measuring radiation activity may also be utilized. Then, utilizing systems and methods of the present disclosure, information obtained by those sensor(s) may then be used to measure, determine or estimate the amplitude of a radioactive source in the body over a period of time of interest, in addition to the location and/or volume of a radioactive source. Such information may also be used to estimate a dose of radiation to surrounding tissue. Such information can also be used to quantify uptake or delivery of radiopharmaceuticals in a tumor or organ, quantify change in uptake or delivery over time (either over the course of a single treatment or by comparison of multiple sessions over hours, days, weeks, months or years), and/or quantify such uptake or delivery in two or more parts of the body to determine useful comparison measurements (e.g., comparisons between hemispheres of the brain, etc.).

SUMMARY

In some embodiments, a method for the ex vivo real-time detection over a period of time of radiation emitted by a subject from the administration of a radioactive analyte that decays in vivo is presented, wherein the method may include applying one or more ex vivo radiation measurement sensors proximate to a point of administration on the subject of the radioactive analyte, and detecting radiation over a desired period of time and producing signal data associated with the desired period of time. The measurement sensor may have at least one sensor output for such signal data, and outputting the signal data. The signal data may be processed using a computer processor in operative communication with a non-transient memory and the measurement sensor output, and more particularly, may receive the signal data associated with the desired period of time, use a measured value of radioactive material proximate the point of administration at a time t to estimate a function of radioactive material proximate the point of administration from a time of administration to the time t based on the signal data associated with the desired period of time, and determine, based on the estimated function of radioactive material proximate the point of administration, an amount of radioactive material disposed in body tissue proximate the point of injection from the time of administration to the time t. In some embodiments, the method may include the step of amplifying the signal data using a signal amplifier in operable communication with the radiation sensor.

In some embodiments, the measured value of radioactive material proximate the point of administration at time t may be measured using an array of two or more ex vivo radiation measurement sensors. In some embodiments, the array may have a known geometry and relative distances between the sensors may be known. It may then be possible, according to some embodiments, to determine a distance from the array (and/or each sensor of the array) to a radiometric center of the radioactive material to estimate a location in the body of the radiometric center of the radioactive material over a period of time. In some embodiments, the array may be used to determine a volume associated with the radioactive material over a period of time. In some embodiments, it may also be possible to estimate a dose of radiation to an area of tissue proximate the radioactive source (i.e., the dose to an area or volume of affected tissue).

In alternative embodiments, a system for the ex vivo real-time detection over a period of time of radiation emitted by a subject from the administration of a radioactive analyte that decays in vivo is presented. The system may include at least one ex vivo radiation measurement sensor to detect radiation over a desired period of time and to produce signal data associated with the desired period of time, and the ex vivo measurement sensor may be adapted to sense radiation proximate a point of administration on the subject of the radioactive analyte. The system may also include a signal amplifier that may be in operable communication with the gamma radiation sensor. The signal amplifier may be adapted to amplify the signal data, and the measurement sensor may have at least one sensor output for such amplified signal data. The system may also include at least one computer processor and a non-transient memory, where the computer processor may be in operable communication with the non-transient memory and the measurement sensor output port.

In some embodiments, the non-transient memory may include computer program code executable by the at least one computer processor, and the computer program code may be configured for performing the steps of receiving the amplified signal data with the desired period of time, accessing a measured amount of radioactive material proximate the point of administration at a time t, and using the amplified signal data, estimating a function of radioactive material proximate the point of injection as a function of time from a time of injection to time t. The system may also, in some embodiments, include a step of convolving the estimated function with a known impulse response from a typical bolus injection. The system may also calculate a correction factor to be applied to one or more measurements made using a nuclear imaging device.

In some embodiments, the system may measure a value of radioactive material proximate the point of administration at time t by using an array of two or more ex vivo radiation measurement sensors. In such embodiments, the array may have a known geometry and have known relative distances between the sensors such that a distance from the array to a radiometric center of the radioactive material being measured may be determined. The system may also determine a volume of the radioactive material being measured.

In certain other embodiments, a method for the ex vivo real-time determination over a period of time of one or more of the magnitude, location, and volume of radioactive material in the body by measuring radiation that decays in vivo emitted by a subject is presented. The method may include the steps of applying one or more ex vivo radiation measurement sensors to or proximate an area of interest on a patient, and detecting radiation over a desired period of time and producing signal data associated with the desired period of time. The method may also include amplifying the signal data using, for example, a signal amplifier that may be in operable communication with the radiation sensor. The measurement sensor may include at least one sensor output for such amplified signal data, and may also output the amplified signal data.

In some embodiments, the amplified signal data may be processed using, for example, a computer processor in operative communication with a non-transient memory and the measurement sensor output, and the processor may perform the steps of receiving the amplified signal data associated with the desired period of time, and comparing the amplified signal data to a set of expected signal data for radioactive sources of various magnitudes, locations, and volumes. The method may also include determining one or more of a magnitude, location, and volume of the radioactive source in the body over the desired period of time by, in some embodiments, fitting the amplified signal data to the most likely set of expected signal data. In some embodiments, the method used to fit the most likely magnitude, location, and volume of the radioactive source in the body may be the Maximum Likelihood Expectation Maximization method.

In some embodiments, the method may include the step of determining a dose of radioactivity to an area of tissue proximate the location of the radioactive source. The method may also include the step of using the determined one or more magnitude, location, and volume of radioactive source in the body to make one or more of a clinical decision or diagnosis.

In some embodiments, the method may include use of an array that may include two or more of the ex vivo radiation measurement sensors, and may also have the sensors disposed in a substantially symmetric geometry about the radioactive source in the body. The sensors may also be disposed proximate one or more desired measurement locations, and in some embodiments, each desired measurement location may include at least a first sensor disposed relatively closer to the radioactive source than a second sensor.

In some embodiments, the method may be used to determine one or more of a magnitude, location, or volume for two or more radiation sources in the body. When desired, the method may also include the step of comparing the one or more determined magnitude, location, or volume of the two or more radioactive sources, and making a clinical decision or diagnosis based on the comparison. The method may also make a clinical decision or diagnosis based on one or more prior determinations or comparisons of the subject patient, and/or using a comparison to a table or other source that includes data from a population of other patients.

DETAILED DESCRIPTION

Figure 1:
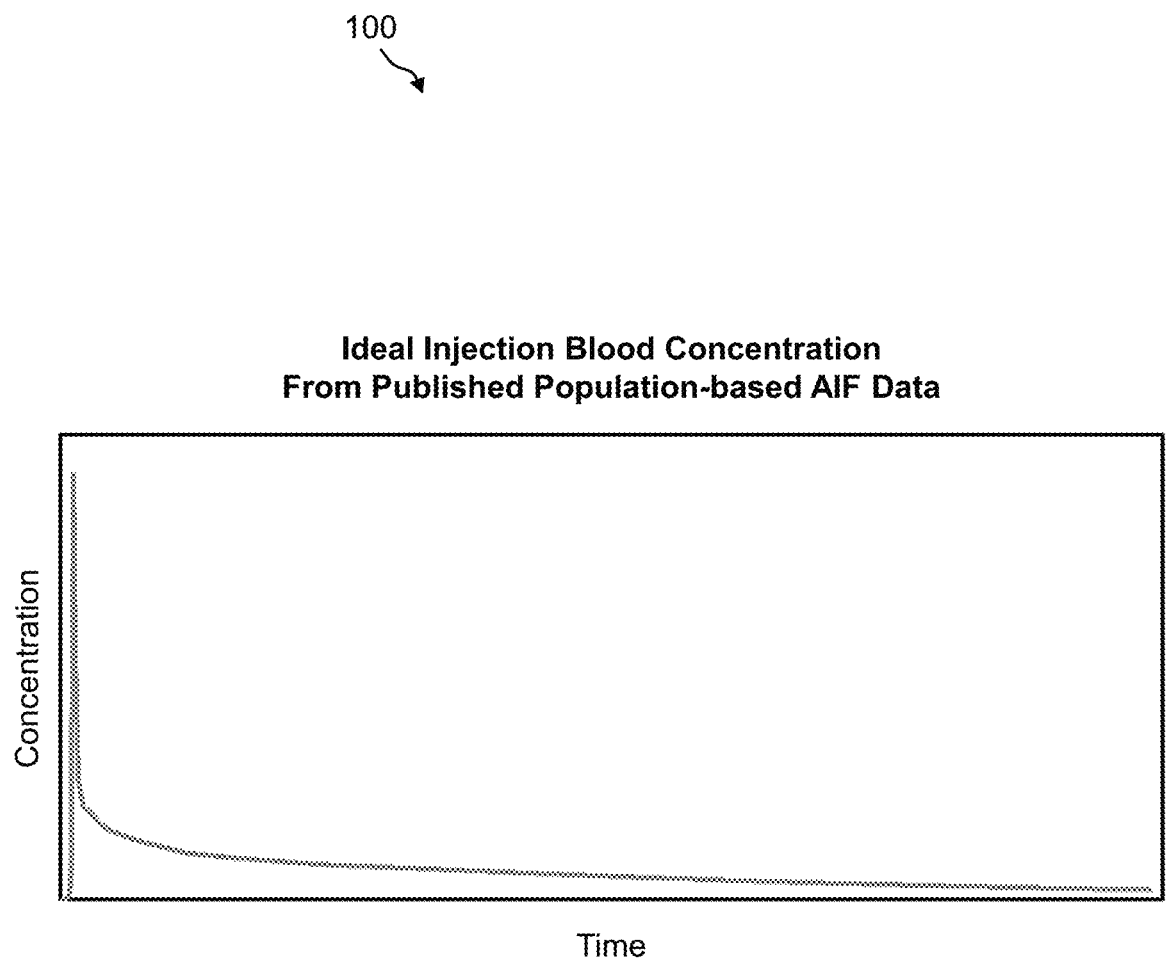
FIG. 1 is a chart illustrating an exemplary injection blood concentration showing concentration vs. time.

The present disclosure teaches, among other things, systems and methods for using measurements of localized radiation to estimate the magnitude, location, and/or volume of radioactive source materials in the body. In some embodiments, such measurements may be repeated at various points in time to determine temporal changes in magnitude, location, and/or volume of radioactive materials in the body. In some embodiments, such information may be used to correct for non-bolus injections of radiopharmaceuticals. Such systems and methods may allow physicians to better measure, for example, cancer treatment effectiveness. In other embodiments, the systems, devices and methods may be used to validate organ dosimetry, or measure uptake of radiopharmaceuticals in tumors, organs or other areas of interest directly.

According to a first set of embodiments, and as introduced above, the SUV of a tumor—for example, the ratio of the amount of radio-labeled tracer in an area of interest compared to the level in the rest of the body—may be calculated using, among other things, molecular imaging data. In general, SUV may be approximated as the integral of concentration of radiotracer in the bloodstream, multiplied by a constant K, plus a variability of distribution volume factor ($V_d$). In the exemplary equation below, $C_T(t)$ represents the concentration of radiotracer in the tumor, $C_B(t)$ represents the concentration of radiotracer in the blood, K is a constant and $V_d$ is a dimensionless volume of distribution equivalent to a volume of blood that contains the same activity as 1 mL of tissue.

$$C_T(t) = K \int_0^T C_B(t)dt + V_d$$

When the injection of radiotracer into the patient goes according to plan (i.e., there is no infiltration or extravasation during the injection and the entire dose of radiotracer goes promptly into the patient's bloodstream), the concentration of radiotracer in the blood can be assumed as the arterial input function. The arterial input function or "AIF" may be referred to as the impulse response for a typical bolus injection, and such impulse responses have been well-studied and measured. When the concentration of radiotracer in the blood cannot be assumed to be a typical bolus injection of known dosage, but instead varies over time as an infiltrated portion of a dose relatively slowly finds its way to the bloodstream, the measured concentration of radiotracer in the tumor becomes a function of both the radiotracer in the bloodstream from the initial (partial) bolus injection, and the later added radiotracer from the infiltration portion. Further, because the magnitude (i.e. the activity) of the infiltration depends on the nature of the infiltration itself (i.e. varies from infiltration to infiltration based on, for example, size of the infiltration, location of the infiltration, local tissue vascularization, etc.), the effective dose into the bloodstream from the bolus portion may be reduced by an unknown amount. The SUV of an area of interest (e.g., a tumor) is therefore altered by an amount proportional to the ratio of the bolus injection integral from a typical injection and the non-bolus injection integral, and may be expressed in some embodiments as follows (where $SUV_b$ is the SUV in the case of a typical bolus injection and $SUV_i$ is the SUV in the case of an infiltrated injection):

$$\frac{SUV_i}{SUV_b} \cong \frac{C_{Ti}}{C_{Tb}} \cong \frac{K \int_0^T C_{Bi}(t)dt + V_d}{K \int_0^T C_{Bb}(t)dt + V_d}$$

In general, the kinetics of radiotracer uptake can be considered a time-invariant linear system. In this exemplary case, a bolus injection could be the impulse and the normal AIF curve (i.e. concentration of radiotracer in the blood as a function of time) could then be the impulse response. The AIF for a typical bolus injection has been well-studied and measured, such that results and applicable measurements are readily available in the literature. Referring now to FIG. 1, an exemplary AIF curve 100 for an ideal injection is presented, showing concentration of radiopharmaceutical in the blood on the y-axis vs. time on the x-axis.

Figure 2:
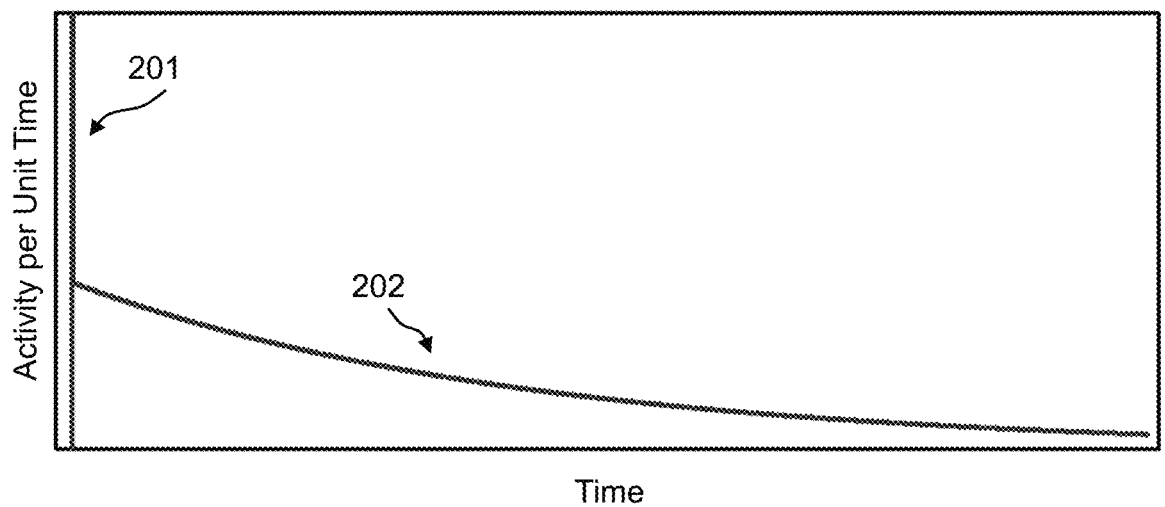
FIG. 2 is a chart showing an exemplary activity entering circulation as activity per unit time vs. time.

In the case of an extravasated or infiltrated injection, however, the AIF may be modeled as a convolution of the normal impulse response with the altered input signal that may comprise a decreased initial impulse (the bolus) followed by prolonged decaying exponential reabsorption. The reduced bolus portion may represent the amount of radiotracer that enters circulation immediately. The extended infusion portion may result from sequestered or infiltrated radiotracer being reabsorbed into circulation through, for example, the venous or lymphatic systems. Referring now to FIG. 2, an exemplary graphical representation of a non-typical injection 200 (e.g., one having an infiltration) is presented, where the activity measured per unit time (y-axis) is expressed as a function of time (x-axis). As illustrated, there is an initial "spike" 201 corresponding to the bolus portion, followed by a gradual decaying exponential reabsorption portion 202.

Figure 3:
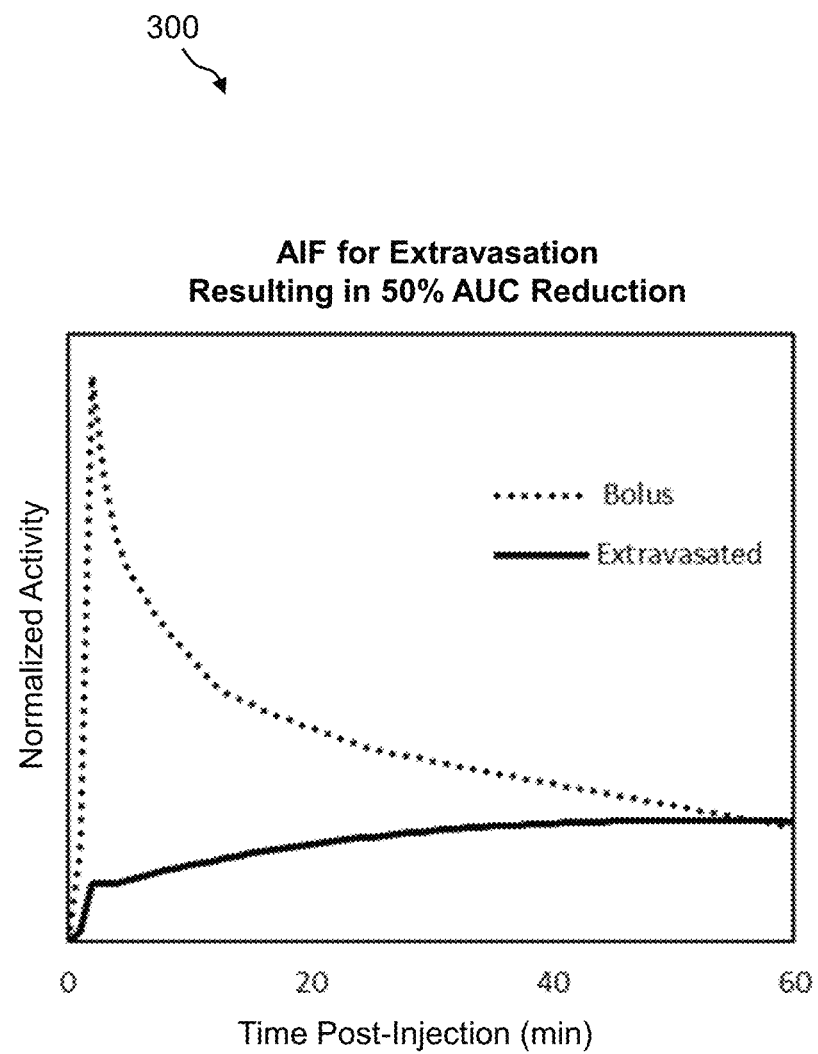
FIG. 3 is a chart showing an exemplary depiction of AIF for Extravasation resulting in a 50% AUC reduction.

In cases of infiltration/extravasation, the injection is not a bolus, and thus the input to the linear system is not an impulse. If the true input to the linear system from an extravasated or infiltrated injection is known or can be determined, it may be possible to then calculate how the altered injection shape may impact the scan metrics such as, for example, SUV (e.g. from a PET scan). For example, it is possible to take the altered linear system input following an infiltrated or extravasated injection and convolve it with the known impulse response from a typical bolus injection, thereby yielding the anticipated blood concentration over time for the infiltrated (i.e. extravasation) injection. That convolution of functions can yield a function for concentration of radiotracer in the blood as a function of time (i.e. the Arterial Input Function or AIF) for any case of infiltration or extravasation. Referring now to FIG. 3, an exemplary graphical representation of an ideal bolus injection AIF (dotted line) alongside an AIF for an extravasation resulting in a 50% SUV (i.e. Area under the curve or AUC) reduction is presented.

To perform the methods outlined above, a user may need to know the amplitude (i.e. the activity) of the infiltration as well as the rate of reabsorption of the infiltrate (so as to produce the function of radiotracer entering circulation over time). One method of determining the amplitude of radioactivity in a particular region (e.g., the infiltration site) is to use nuclear medicine imaging data taken during an imaging session, which may yield an amplitude in a region at a time=t. This alone, however, cannot enable one to extrapolate the infiltrated amount at the time of injection (t=0), or the rate at which the radiotracer may have been reabsorbed into the bloodstream.

Figure 4:
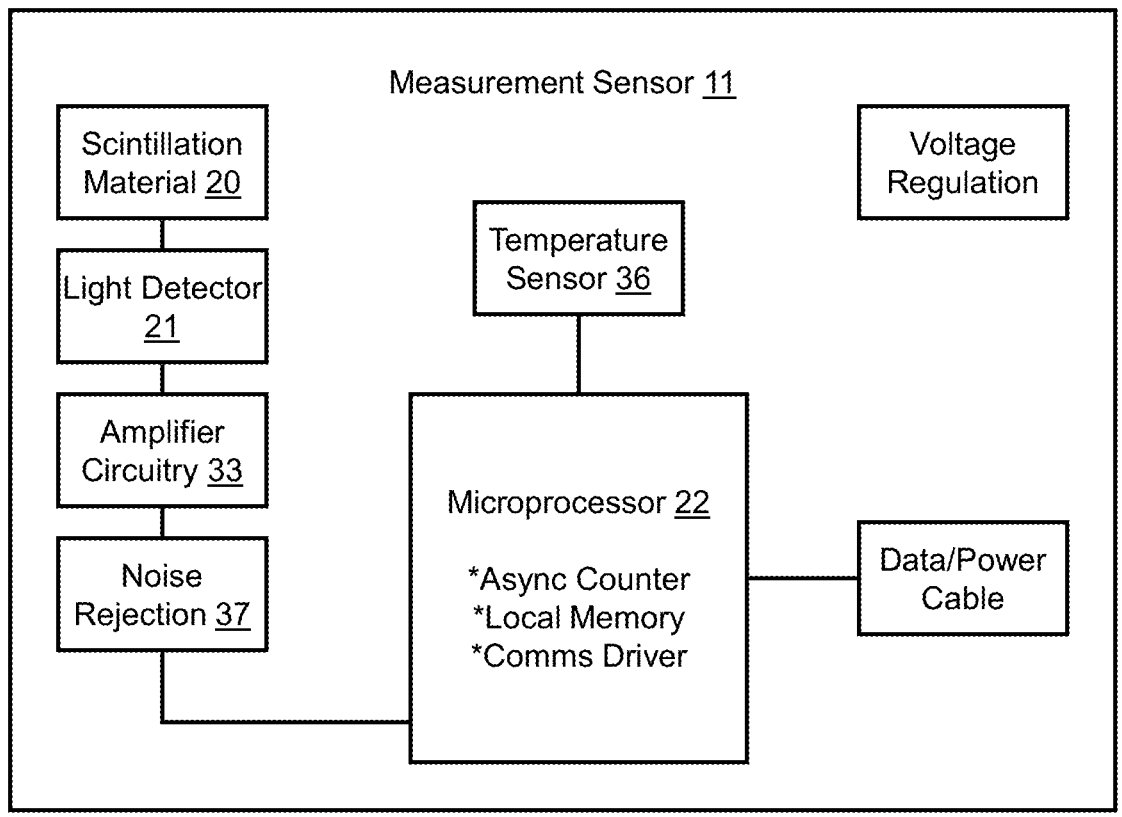
FIG. 4 is an exemplary schematic of a measurement sensor according to some embodiments of the present disclosure.
Figure 5:
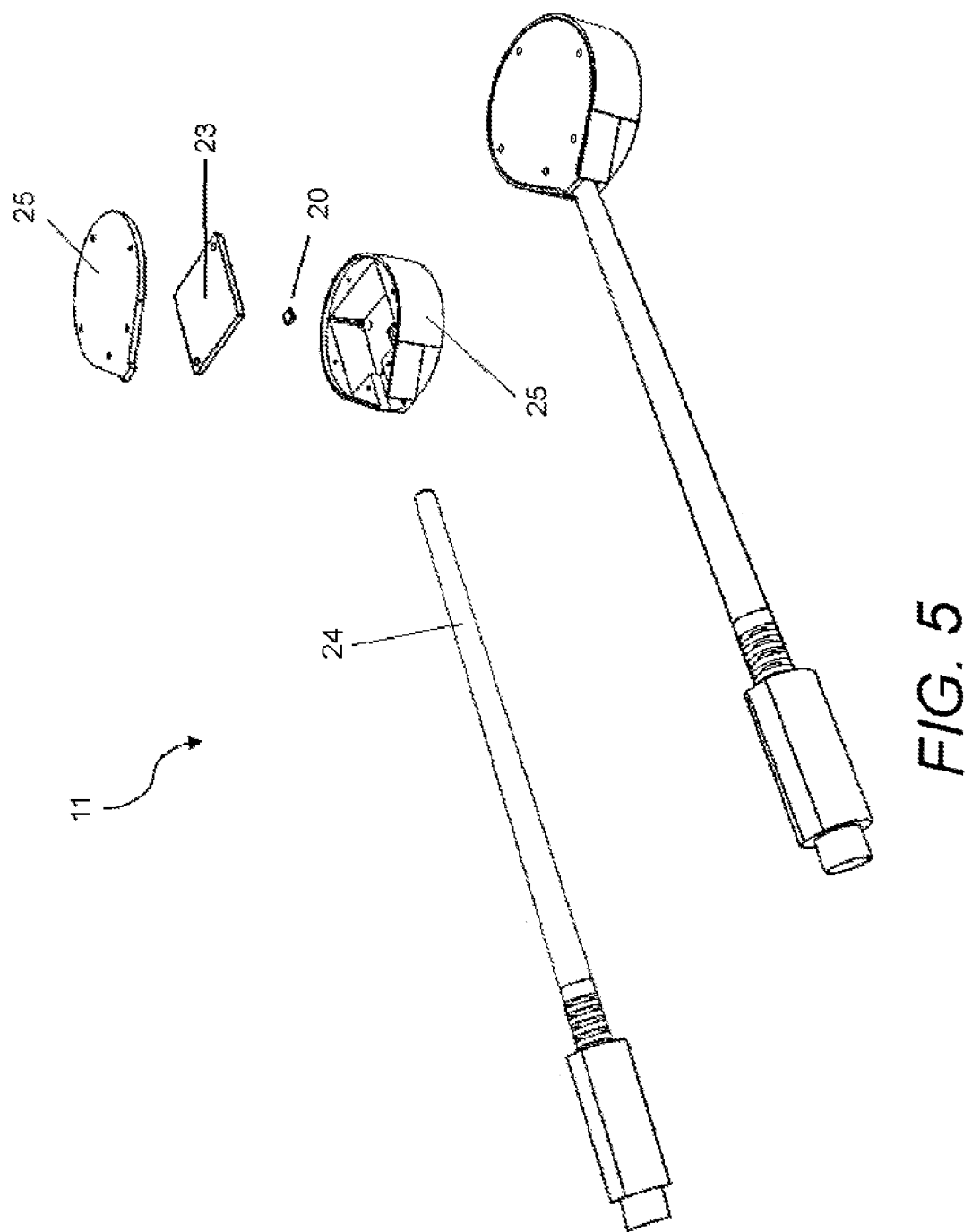
FIG. 5 is an exemplary illustration of a measurement sensor according to some embodiments of the present disclosure.
Figure 6:
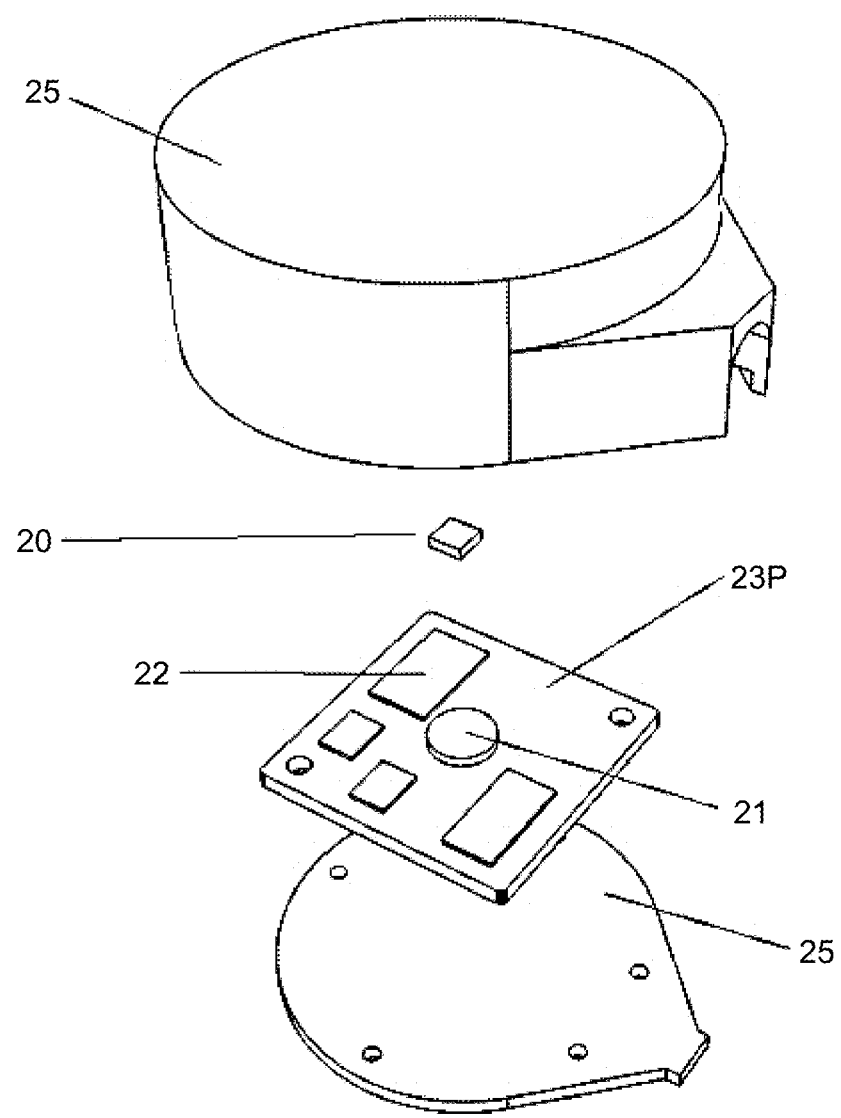
FIG. 6 is an exemplary illustration of a measurement sensor according to some embodiments of the present disclosure.

In some embodiments, localized radiation detectors such as those disclosed U.S. Pat. Nos. 9,939,533 and 9,002,438 may be used to measure activity at the injection site as a function of time (i.e. time-activity curve or TAC). Referring now to FIGS. 4-6, a measurement sensor 11 may be utilized that may include, for example, a scintillation material 20; a light detector 21; and a sensor processor 22 with associated non-transient sensor memory 30, logic or sensor software 26, and other circuitry supporting these components in operable communication, optionally with a printed circuit board 23P (FIG. 6). Such sensors may also include amplifier circuitry 33 and/or a temperature sensor 36. Measurement sensor 11 may utilize a scintillation material 20 to receive gamma radiation from positron emission decay and convert the radiation into photons, such as pulses of light, which may then be detected by the light detector 21. The sensor processor 22 may enable measurement and collection of the photons, such as the number of light pulses detected over a given amount of time. Optionally, noise rejection 37 may be included that may provide a filter for filtering amplified signal data based on the height or amplitude of such pulses. For example, noise rejection 37 may include a voltage comparator or an analog to digital converter with computer program code to compare the digital output to a reference level.

Possible scintillation materials 20 include, but are not limited to: Bismuth Germanate (BOO); Gadolinium Oxyorthosilicate (GSO); Cerium-doped Lutetium Oxyorthosilicate (LSO); Cerium-doped Lutetium Yttrium Orthosilicate (LYSO); Thallium-doped Sodium Iodide (NaI(T1)); Plastic Scintillator (Polyvinyltoluene); or Cadmium Zinc Telluride (CZT). In an exemplary embodiment of a measurement sensor 11, multiple scintillation materials 20 adapted to measure different radioisotopes may be used. In another embodiment of a measurement sensor 11, scintillation materials 20 that do not require the use of a light detector 21 may be used. In another embodiment of a measurement sensor, multiple scintillation materials 20, each with their own detection circuitry, may be included to enable a two or three dimensional array of measurements. In some embodiments, the sensor(s) are capable of detecting alpha particles, beta particles, x-rays, gamma rays, and/or other particles/energy indicative of radioactive material.

Of course, other radiation sensors known in the art may be utilized as desired. For example, radiation sensors capable of detecting alpha particles, beta particles, x-rays, gamma rays or any other kind of radioactive decay particle/energy may be utilized depending on the desired application. Measurement of beta particles, for example, may be advantageous when assessing delivery of a radio-therapeutic to an area of the body as such drugs sometimes release beta particles. It may similarly be advantageous to ensure that certain beta particle (or other particle) emitting drugs or other substances not be reaching a certain part of the body. Thus, sensors could be used to confirm the absence of such substances. All that is typically necessary for the sensors, in some embodiments, is that the sensor be capable of detecting emissions from radioactive material, and further capable of transmitting or otherwise sharing information about those emissions to the system for processing. It may also be desirable, in some embodiments, that the sensors and/or system generally be able to measure an energy level associated with the detected emissions, or filter received energy above or below a certain threshold.

Figure 7:
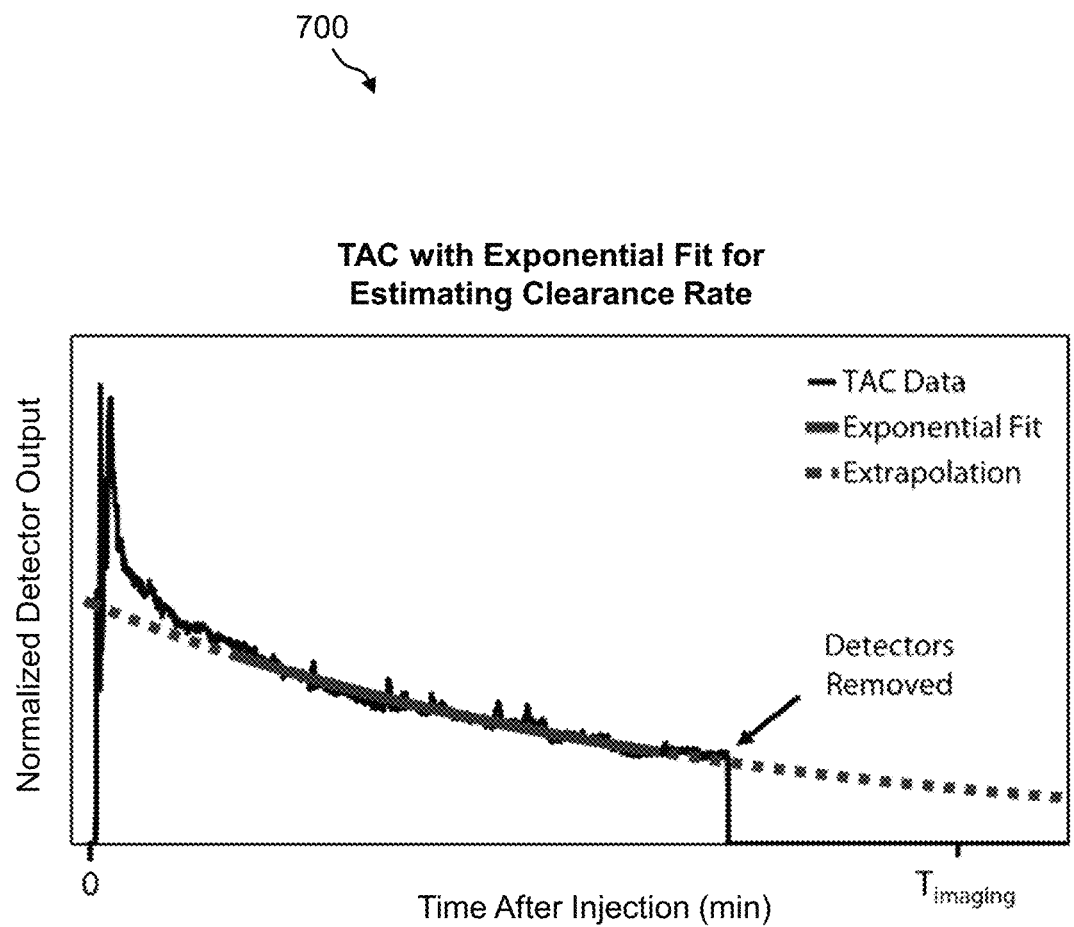
FIG. 7 is an exemplary chart showing a time activity curve (TAC) with an exponential fit for estimating a clearance rate.

Utilizing measured data, the rate of reabsorption into the bloodstream may be calculated by observing the activity at the detector as a function of time (i.e. the rate at which radioactive activity leaves the infiltration site). Knowing from the TAC the amount of radioactive material at a time t, and the rate at which it left the infiltration site, an estimate of the initial amount of radioactive material infiltrated may be determined. Knowing this information, the altered injection curve and the reduction of the initial bolus may be plotted, and a function of concentration of radiotracer in the blood as a function of time determined. With that function known, a correction factor for SUV or the like may be applied and the clinician may better diagnose treatment efficacy, etc. Referring now to FIG. 7, an exemplary TAC with Exponential Fit Curve is presented.

As introduced above, the many constraints on nuclear imaging apparatus (e.g. PET scanners) such as availability, cost, operational resources, etc., make determining the size and/or magnitude of a radioactive source in the body using such apparatuses not always possible. For example, taking a measurement of an infiltration area that may otherwise be outside the field of view and/or otherwise not of interest at the time of the scan is not always feasible. It would also be advantageous to have an understanding of the magnitude and scope of any infiltration from the time of the injection forward, rather than having to wait until the patient is moved to the scanner. The ability to determine the magnitude of an infiltration without using a nuclear imaging scanner may also be desirable because it could eliminate the need to use such a scanner at all where the scope of the infiltration is deemed large enough to render a scan unproductive, thereby saving the patient from additional unnecessary radiation exposure (e.g., from a computerized tomography (CT) scan, or the like).

It may also be advantageous to measure the area and/or magnitude of radioactive material uptake in an area of interest generally, without having to depend on the availability of more complex and expensive nuclear imaging apparatuses. To determine the efficacy of a treatment to eliminate a tumor, for example, a physician may want to know whether the tumor is shrinking over a period of time (e.g., days, weeks, months, etc.). Requiring a patient to undergo successive nuclear imaging scans and face exposure to the requisite radiation on multiple occasions is, at best, not ideal, and in some cases is prohibitory.

One way to overcome the difficulties outlined above is, for example, to utilize multiple detectors that may be arranged in a known geometry. Each sensor may measure radioactivity coming from a given source of material, and each sensor may have a known sensitivity thereby enabling it to provide information about intensity measured for each event. Such intensity may depend, for example, on the sensor's distance from the source, material-specific attenuation between source and sensor, as well as intensity of the source itself. As noted above, a determination of each sensor's distance from the source may not be determinable on a sensor by sensor basis because the measured intensity at any given distance depends on an unknown intensity at the source. However, by utilizing data from an array of sensors, and measuring intensity of the same area of different but known relative distances, information regarding both magnitude, location, and/or size of the source may ultimately be determined at each unit of time.

In some embodiments, and as just one example, a method known as trilateration may be used in combination with the disclosures herein to determine the distance of each sensor from a "radiometric center." Trilateration is similar in some respects to triangulation but utilizes distance instead of angles. In some embodiments, each sensor could calculate an estimated distance R to the source based on the measured intensity of each count. The direction of the source, however, would be unknown. Thus, the determined distance dictates only that the source must lie somewhere on a sphere of radius R centered about the sensor. Having such a sphere for multiple sensors (e.g., four) positioned in 3-D space, however, a point where the four spheres intersect could identify the radiometric center of the source material, and allow for the system to know the distance between a radiometric center of the source material and the sensor.

Figure 8:
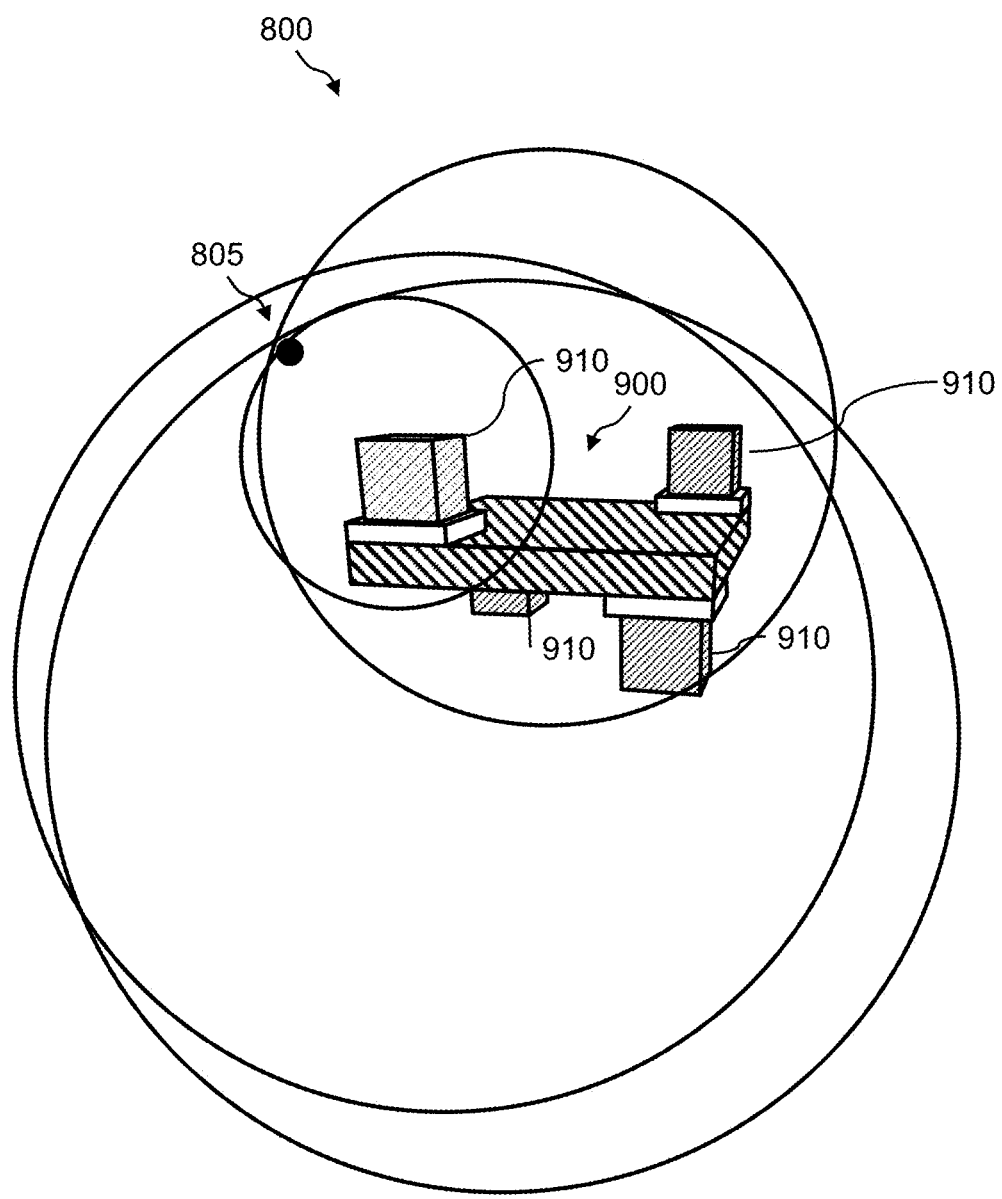
FIG. 8 is an exemplary illustration of a sensor configuration according to some embodiments of the present disclosure.

Referring now to FIG. 8, an exemplary representation of one trilateration model is presented according to some embodiments. In this exemplary embodiment, and with further reference to FIG. 9, a set of sensors 910 may be disposed in a known three-dimensional configuration. Because both distance and source intensity would be unknown, an iterative process may be utilized to determine values that satisfy the system's given constraints. For example, various parameters could be employed to determine the values wherein the highest number of spheres best intersect. Certain assumptions may be employed including estimates for expected activity, assumptions about the material-specific attenuation between the source and each sensor, and distance range approximations to aid the iterative process. While measurement noise could make finding exact intersection points difficult, a best fit may be employed to ultimately find a sufficiently precise distance estimate, and determine an estimate for a radiometric center (e.g., point 805). Knowing this distance, the system could then calculate the amount of radioactive material present based on the intensity of the measurements at any given time (including situations where the source at a time $T_2$ has shifted relative to an earlier time $T_1$).

Various different sensors capable of measuring counts in the presence of radioactive material are available and known in the art. These include, but are not limited to: the sensors disclosed hereinabove with reference to FIGS. 4-6; TLD—thermo-luminescent device; OSL—optically stimulated luminescence device; Radiation sensitive film; RADFET—radiation sensitive field-effect transistor; PIN Diode—radiation sensitive diode; Ionization chamber; Geiger counter; and Scintillation crystals, among others. It will be appreciated that the array of sensors discussed herein may be of one type or may be a combination of different types if desired. The system need only know the relative sensitivity of each sensor to appropriately calibrate the measurements.

As noted above, the relative geometry of the sensor array must be known, but that geometry is otherwise generally unrestrained, both in space and time. In some embodiments, so long as the relative geometry of the sensors is known at each time t, the relative distances of each sensor to the radiometric center be determined. Note, however, that in some embodiments it may be necessary that the sensors be disposed in a three-dimensional array, rather than all residing, for example, on a similar two-dimensional plane, or in a one-dimensional line.

Figure 9:
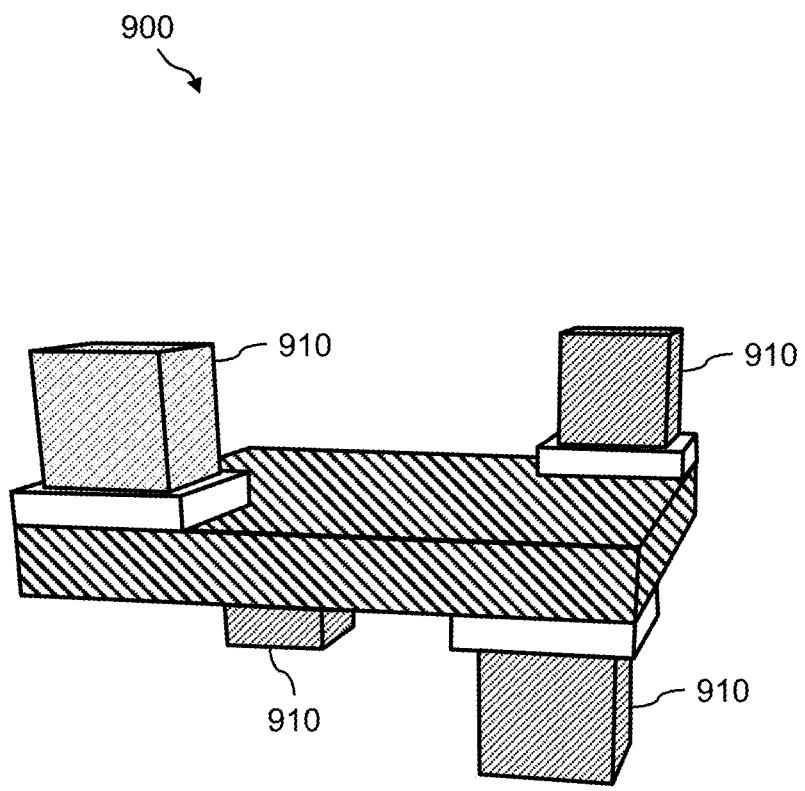
FIG. 9 is an exemplary illustration of a sensor configuration according to some embodiments of the present disclosure.
Figure 10:
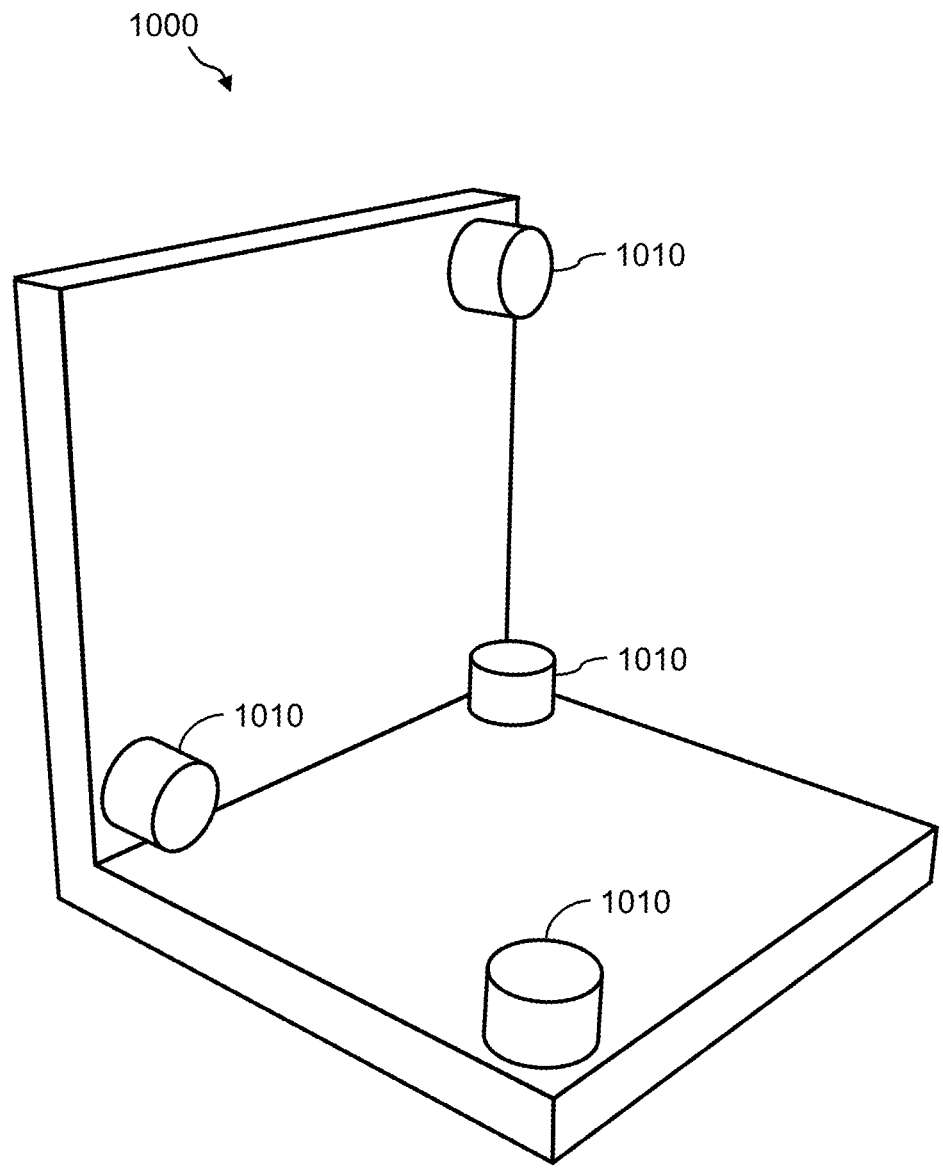
FIG. 10 is an exemplary illustration of a sensor configuration according to some embodiments of the present disclosure.

Referring now to FIG. 9, an exemplary four-sensor array is presented according to some embodiments. As illustrated, the various sensors 910 may be arranged in a three-dimensional configuration. In certain other embodiments, and with reference to FIG. 10, various sensors 1010 could be disposed in a three-dimensional L-bracket configuration. FIGS. 9 and 10 represent just two of many different potential sensor arrangements and geometries that may be utilized.

In some embodiments, the various sensors discussed herein that may be arranged in an array to determine a radiometric center of a radiation source that may be the same sensor(s) that measure the time-activity curve (TAC) discussed above. Accordingly, as disclosed herein, the sensors may be utilized to detect an infiltration, measure the time-activity curve at the injection/infiltration site, and even measure the magnitude of the infiltration so as to yield information about the SUV, for example, of an area of interest (e.g. tumor) ultimately measured by a nuclear imaging device (e.g., PET scan) and any correction factor that may need be applied in view of, for example, an imperfect injection of radiotracer.

Figure 11:
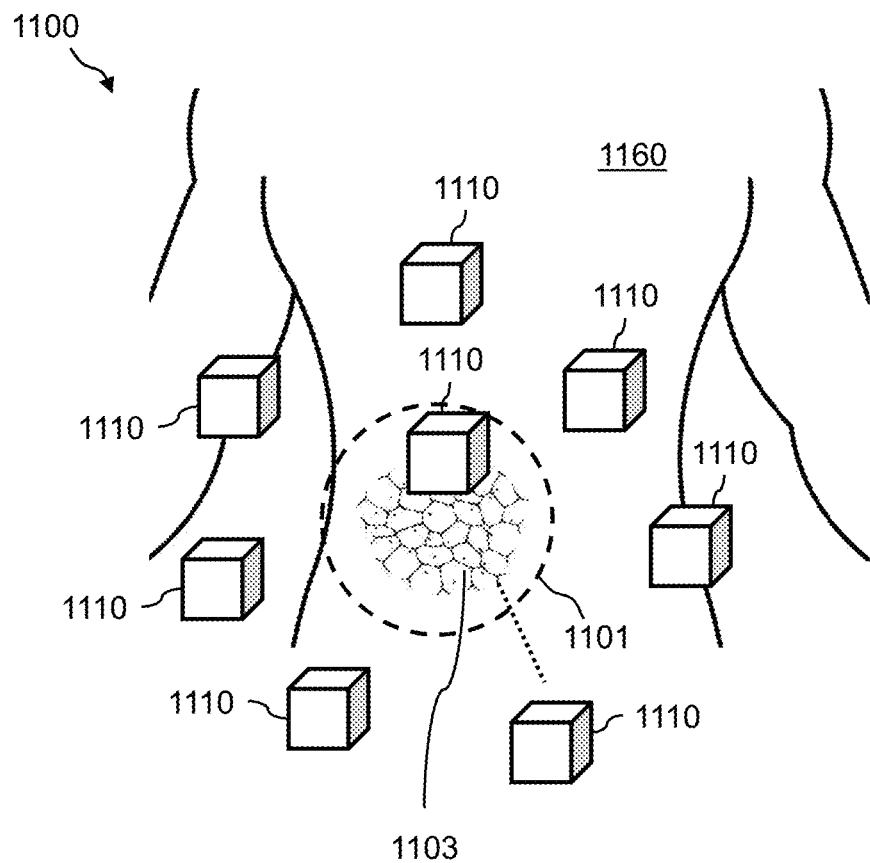
FIG. 11 is an exemplary sensor configuration according to some embodiments of the present disclosure.

In certain other embodiments of the present disclosure, the system may utilize arrays of sensors in combination with other estimation techniques to, for example, quantify and/or measure the magnitude and/or location/size of a radioactive area of interest. In some embodiments, and referring now to exemplary FIG. 11, an area of interest 1101, which may contain a volume of radioactive source material 1103, may be surrounded by a one or a plurality of sensors 1110, forming a sensor array. The area of interest 1101 may be within, for example, a patient 1160 (e.g., an infiltrated radiopharmaceutical injection, a tumor being treated with radiopharmaceuticals, an organ desired to be dosed with a precise amount of radiopharmaceutical, etc.), but may more generically be any volume of area that may include radioactive material, whether located in a body, within some other container/vessel, or standing alone. In this exemplary embodiment, the sensor(s) 1110 may be positioned outside the body of patient 1160 in various geometries relative to the area of interest 1101.

The array of sensors 1110 may include any number of sensors, including in some embodiments as few as one or two, or as many as four, eight, ten, twenty, thirty, fifty, one-hundred, or more or anywhere in between. Further, each of the plurality of sensors 1110 that make up the array may be identical sensors to one another, or one or more may have unique characteristics relative to one or more other of the sensors 1110. Such distinguishing characteristics may include, but are not limited to, different shielding configurations, different energy threshold settings for detection, different size/shape for given locations or applications, etc. Other varying characteristics may also be utilized, some of which are discussed in greater detail elsewhere in this disclosure.

In some embodiments, each sensor 1110 may detect particles/energy emitted from the radioactive area of interest 1103. In some embodiments, the sensors 1110 may detect the emitted particles as discussed hereinabove (e.g., through use of scintillation material that emits light when impacted with radioactive particles (e.g., alpha particles, beta particles, or the like) in the sensor and circuitry capable of counting the number of "hits" per unit time). As noted above, however, other sensor configurations and detection methods may be used.

In general, the array of sensors 1110 may be arranged in any desired geometry relative to each other and relative to the area of interest 1101. In some embodiments, it may be advantageous to utilize a known geometry of sensors, and it may be further advantageous to arrange the sensors 1110 such that the location of each sensor 1110 may be known relative to each of the other sensors 1110 in the array.

Using techniques known to those having skill in the art, it is possible to estimate the radioactive activity expected at a given location (e.g., at the location of a specific sensor 1110) given certain information, including for example a known amount of radioactive material centered about a known point in space. For example, if the radiometric center, and amount and type of radioactive material is known, and information about the density and composition of the material through which the emitted particles will pass to reach the sensor 1110 (e.g., water, tissue, bone, etc.), one may determine a likelihood that a particle emitted from the radiation source would be detected at a given point in space. Using these techniques, a set of expected measurements can be generated for radioactive sources of various magnitudes, locations, and volumes.

Accordingly, by inversing such calculations, measurements of activity taken at various points in space relative to a source of radioactive material may be used to estimate characteristics about the radioactive material source itself, for example, magnitude, location, volume, etc. In one example, activity at various locations about a radioactive source may be measured as a function of time. Then, knowing the likelihood of measuring the activity actually measured relative to radioactive sources of various magnitudes and locations, a least squares regression analysis may be used to estimate the magnitude, location, and/or volume of the actual radioactive material source. Using such techniques, and assuming a distribution, for example Gaussian, of radioactive material, an accurate determination of the amount of radioactive material present can be determined (i.e., the magnitude), and the radiometric center of the radioactive material (i.e., location), and/or distribution of radioactive material (i.e., size of the source of radioactive material) may be determined.

According to one exemplary method of using the system disclosed herein, and referring again to FIG. 11, the system 1100 may assume the presence of a "blob" of radioactive material (e.g., radioactive area of interest 1103) positioned relative to the array made of sensors 1110. The radioactive material's location and magnitude may be unknown, but the radioactive material emits radioactive energy/particles and/or decays into other particles/energy (e.g., alpha particles, beta particles, x-rays, gamma rays, positrons etc.) that may be measured by each of the sensors 1110. In particular, each sensor 1110 may detect those particles that intercept it. In some embodiments, by measuring the energies of the particles, the system may eliminate unwanted "hits" (e.g., deflected particles), and utilize knowledge of the material through which the particles traveled (i.e., water, bone, etc.) to gain an understanding about the magnitude and/or volume (among other things) of the radioactive source.

Having measured the activity of direct "hits" per unit time at each known location, the least squares regression analysis can be applied to find the magnitude (A), mean location ($\mu$) and standard deviation ($\sigma$) of the radioactive source which minimizes the error between actual counts ($c_n$) and estimated counts ($\hat{c}_n$) associated with the various possibilities of radioactive sources. In some embodiments, the system or method may assume a Gaussian distribution of the radioactive material of interest, but other distributions are possible. Knowing such information, it may be possible to diagnose certain conditions, determine a dose of radiation to tissue in the body proximate the radioactive source, analyze whether a desired dosage of therapeutic radiopharmaceutical has been delivered to an area of interest (or is not present in an area of interest or below some acceptable threshold), and by capturing such exact measurements, it may be possible to compare results for a single patient over multiple visits to track efficacy of treatments, etc.

$$\operatorname{argmin}_{A,\mu,\sigma}\left(\sum_{n=0}^{N}(c_n - \hat{c}_n)^2\right)$$

One drawback to this technique may be that the standard deviation of the distribution is sometimes difficult to determine accurately. For example, the counts or "hits" measured by an array made of sensors 1110 may be the same for a collection of radioactive material distributed over a first volume as it would for a collection of the same amount of radioactive material distributed over a second volume. Accordingly, while the magnitude of the source (i.e., how much radioactive material is present) and radiometric center of the source (i.e., the location about which the radioactive source is centered) may be determined, the volume of space that the source occupies may be more difficult to estimate according to some techniques. While magnitude and location can provide significantly advantageous information in some circumstances (e.g., determining the size and location of an infiltration and using that information to aid in interpretation of medical imaging, for example), it is not always sufficient to determine, for example, the radioactive dose to surrounding tissue, as the distribution of the radioactive material (i.e. the standard deviation discussed above) in the tissue would be needed.

Accordingly, it would be advantageous to modify and/or supplement the techniques described hereinabove to determine not only the magnitude and location of a radioactive area of interest (e.g., 1103), but also gain an understanding of the volume/distribution of the material.

Figure 12:
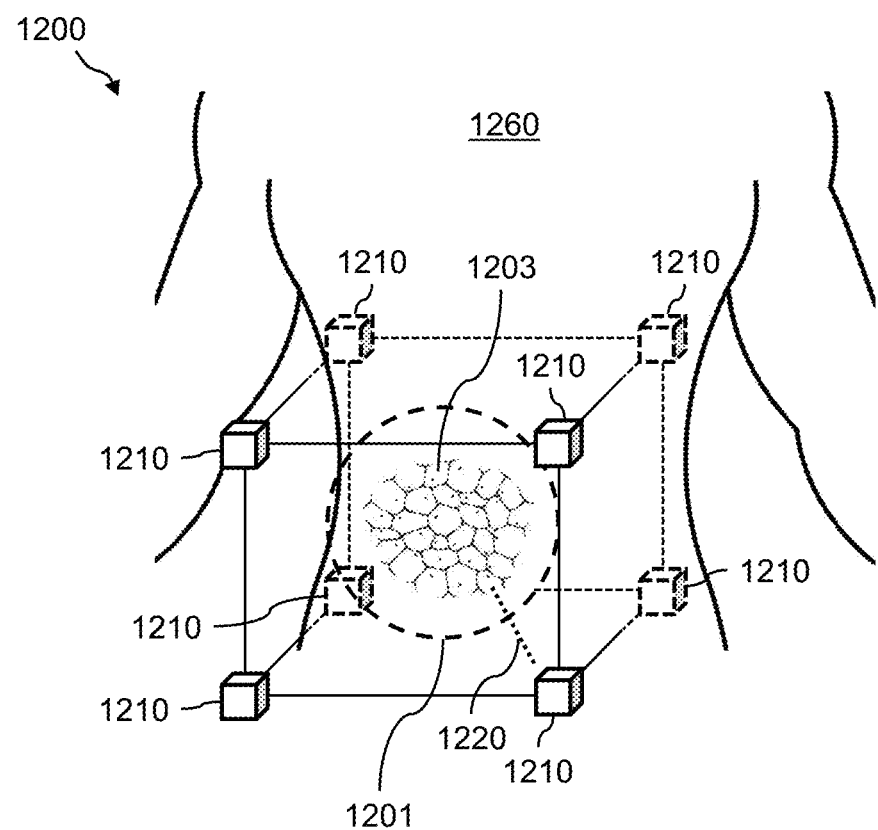
FIG. 12 is an exemplary sensor configuration according to some embodiments of the present disclosure.
Figure 13:
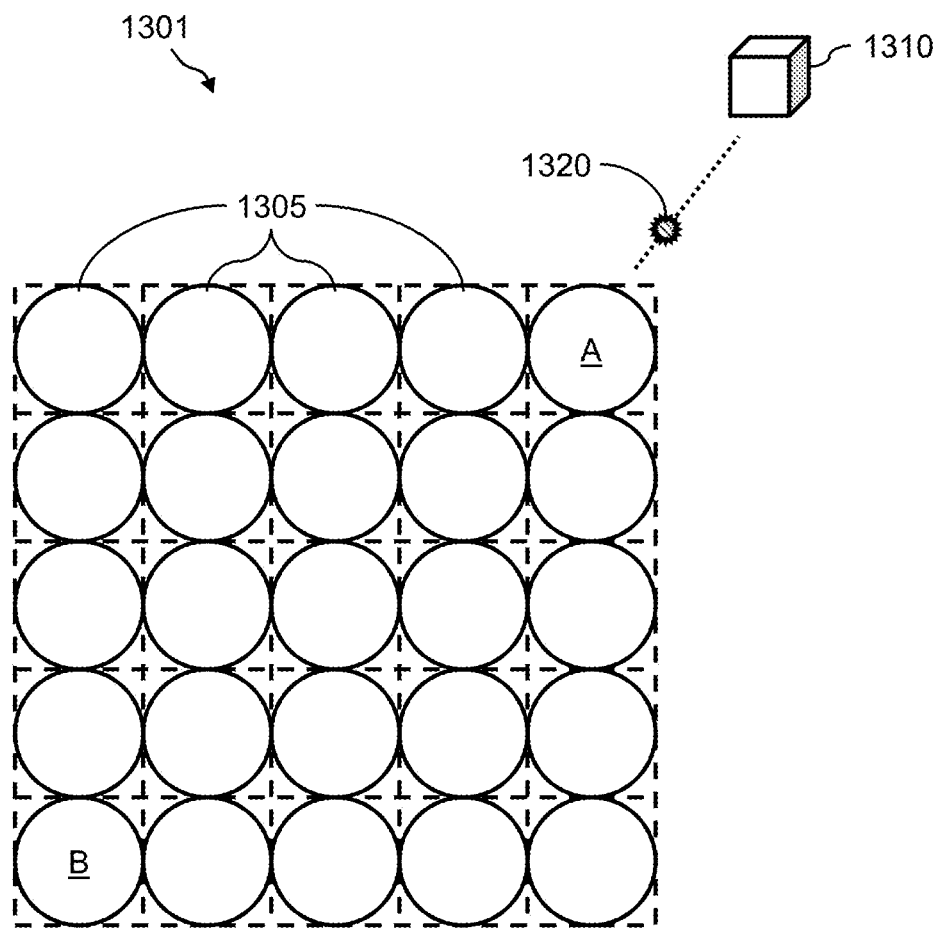
FIG. 13 is a simplified illustration of pixels and a sensor according to some embodiments of the present disclosure.

According to additional embodiments of the present disclosure, sensor arrays not unlike those discussed hereinabove may be used in combination with other methods to obtain even more robust estimates of the magnitude, location, and/or volume of a radioactive area of interest. Referring now to FIG. 12, an exemplary system 1200 is presented where a volume of interest 1201 may be defined and divided into a plurality of three-dimensional "voxels" (analogous to two-dimensional pixels, see FIG. 13 below). In some embodiments these voxels may be of uniform size and shape, while other embodiments may include voxels of varying size, shape, arrangement, etc. Within volume of interest 1201 may lie a radioactive area of interest 1203 of unknown magnitude, location, and volume. Spaced about the volume of interest 1201 may be a plurality of sensors 1210 forming a sensor array.

Similar to the sensor array discussed hereinabove, each of the sensors 1210 may be positioned proximate a known location relative to the plurality of other sensors 1210. The sensors 1210 may be arranged at random known locations about the volume of interest 1201, or in preferred embodiments, may be positioned in mathematically advantageous geometries about the volume of interest 1201, including for example, in triangular, cubic, hemispherical or spherical orientations about the volume of interest 1201, among others. In some embodiments, the arrangements may be symmetrical. In the exemplary embodiment illustrated in FIG. 12, the sensors are arranged in a substantially cubic configuration about area of interest 1201. It should also be understood that in some embodiments, the relative locations of sensors in space may change over time, and techniques could be employed to measure or otherwise determine the relative positions of the plurality of sensors 1210 at each time t.

In some embodiments, a system for estimating the magnitude, location, and volume of a radioactive area within a volume of interest, such as for example the system 1200 illustrated in FIG. 12, may utilize an estimation method known as Maximum Likelihood Expectation Maximization (MLEM). Referring now to a simplified exemplary two-dimensional configuration shown in FIG. 13, MLEM methods may be used to calculate a probability for each cell or pixel 1305 that a particle 1320 having a certain energy measured at a given location (i.e., the location of one of the sensors 1310) originated from each particular cell 1305. Put another way, for each cell 1305, a probability may be determined that a particle 1320 originating from each cell 1305 would arrive at the location of the sensor 1310. Using the same methods, probabilities for each voxel in a three-dimensional space (e.g., volume of interest 1201) can be determined.

For example, and referring again to FIG. 13, consider a sensor (e.g., sensor 1310) positioned at a location relative to an area of interest 1301 divided into a plurality of pixels 1305. Sensor 1310 may receive a "hit" from a particle 1320 emitted by the radioactive material located within the area of interest 1301. Specifically, particle 1320 measured by sensor 1310 may have originated from any one of the pixels 1305.

Particles released from radioactive material travel in random directions from their source, and therefore there is only a chance that any particular particle (e.g., particle 1320) will travel in the direction of a given sensor (e.g., sensor 1310). Further, the greater the distance between the source of the particle 1320 and the sensor 1310, the more likely it is that the particle 1320 will collide with some intervening material (e.g., water molecule, bone, etc.) and scatter to a different trajectory. When scattered, the particles lose energy, and therefore it is possible to calibrate the sensors to disregard scattered particles that may be received at a sensor, if desired, as counting scattered particles may introduce error.

Accordingly, referring again to FIG. 13, the probability that a sensor 1310 is hit by a particle 1320 that originated in cell B may be lower, for example, than the probability that the particle 1320 originated in cell A. This is because, in this example, the physical distance between cell B and the sensor 1310 is greater than the distance between cell A and the sensor 1310, thereby not only reducing the "solid angle" created by the sensor with respect to the pixel, but also introducing a greater chance that the particle will be scattered from its original trajectory by intervening material. Knowing the distances between the sensor 1310 and each pixel 1305, the density and other characteristics of the material(s) through which the particle must travel to reach the sensor 1310, and the characteristics of the radioactive material of interest itself, among other things, the system may determine a set of such probabilities of a particle "hitting" a sensor 1310 for each pixel 1305, and may determine such sets relative to each sensor 1310 for each pixel 1305.

The same is true for a three-dimensional configuration, such as for example the configuration illustrated in FIG. 12. In general, the probability that a particle 1220 counted by sensor 1210 originated from a relatively close voxel within area of interest 1201 is greater than a probability that particle 1220 originated from a relatively distant voxel in area of interest 1201. As above, a set of probabilities for each voxel may be determined for each sensor. This information may be used to generate, or may itself be characterized as, a set of expected signal data associated with radioactive sources of various magnitudes, locations, and/or volumes.

Knowing these probabilities, the system 1200 may be used to take actual measurements of "hits" per unit time observed at each sensor 1210 and estimate, among other things, the magnitude, location, and/or volume of a radioactive source. In some embodiments, because the radioactive material releases particles in all directions, each sensor 1210 should register some number of "hits" if a sufficient amount of radioactive material is present within volume of interest 1201. Each "hit" at each sensor 1210 corresponds to a set of probabilities across the voxels 1205 in the volume of interest 1201 corresponding to the likelihood that the particle (e.g., 1220) intercepting a particular sensor 1210 originated in each voxel 1205. In some embodiments, the system may analyze the sets of probabilities for each "hit" at each sensor 1210 and iterate over time to determine the most likely distribution of radioactive material 1203 within the volume of interest 1201 that would generate the "hits" observed. The system may also iterate over various energy levels, providing additional detail.

Generally speaking, increasing the number of available sensors (e.g., 1210) positioned about the radioactive material source (e.g., 1203) may increase the accuracy with which the system 1200 can estimate the magnitude, location, and/or volume of the source. Similarly, increasing the number of voxels used in the calculations (i.e., more voxels comprising smaller and smaller volumes each) may increase the system's accuracy. However, as the number of sensors and/or voxels increases, the number of required calculations and processing requirements of the system generally increases significantly. It may therefore be advantageous, in some embodiments, to take advantage of certain sensor positioning arrangements that may simplify calculations or aid in the iterative convergence of the calculations, including for example using symmetrical sensor configurations, among other things. Such configurations may also shorten the time and/or reduce the number of calculations required to achieve acceptable iterative convergence. Various distributions of voxel size may also be utilized, such that smaller voxels are utilized closer to and within the radioactive source material 1203 and larger voxels are utilized elsewhere, for example.

Figure 14:
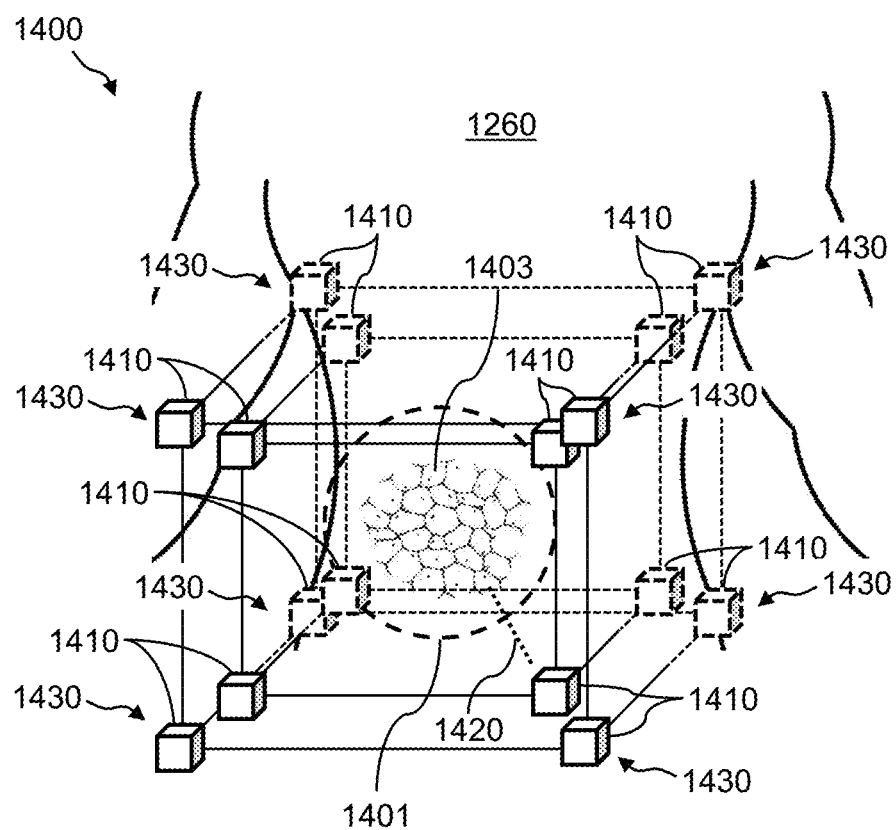
FIG. 14 is an exemplary sensor configuration according to some embodiments of the present disclosure.

In some embodiments, in may also be advantageous to include two or more sensors proximate each of the fixed points about a volume of interest. An exemplary configuration illustrating an exemplary dual-sensor approach is illustrated in FIG. 14. As shown in the exemplary configuration there, a concentric-cubic configuration may be used, where a first set of sensors 1410 may be positioned at each of eight points on a first, inner cube surrounding the area of interest 1401, and a second set of sensors 1410 may be positioned at each of eight points on a second, outer cube surrounding the same area of interest 1201. Proximate each of the eight known points 1430 positioned about the volume of interest 1401, two sensors 1410 may then be provided, for a total of sixteen sensors in the system. Of course, each fixed location 1430 may include more than two sensors 1410 if desired (e.g., a third cube of greater dimensions), and/or any number of fixed locations 1430 may be utilized (including for example, one, two, four, eight, sixteen, twenty-four, or more, or any number in between, as desired). Utilizing two or more sensors 1410 at each location 1430 may have the advantage of aiding, among other things, an iterative convergence. More particularly, by having a second sensor 1410 slightly farther away from the source of radioactive material 1403 relative to the first sensor 1410 at each location 1430, they system may more efficiently arrive at an iterative convergence.

In some embodiments, it may be advantageous to detect particles from plurality of radioactive sources. For example, by introducing two or more radiopharmaceuticals with distinguishable radioactive characteristics (e.g., different energy levels, different uptake rates, etc.), additional information may be detected. Sensors in such systems may be tuned to detect particles of one or more different energy levels, thereby providing additional information. For example, the amount or rate of uptake of one drug associated with a first radiopharmaceutical relative to the amount rate of uptake of a second drug associated with a second radiopharmaceutical may provide useful information to a clinician.

Figure 15A:
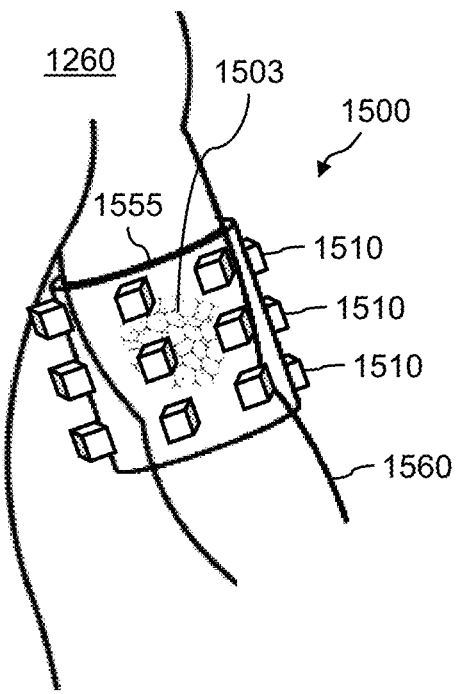
FIG. 15A is an exemplary sensor configuration according to some embodiments of the present disclosure.
Figure 15B:
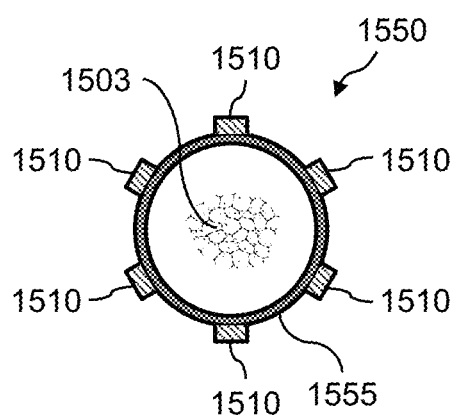
FIG. 15B is another view of the exemplary sensor configuration presented in FIG. 15A, viewed along a longitudinal axis.
Figure 15C:
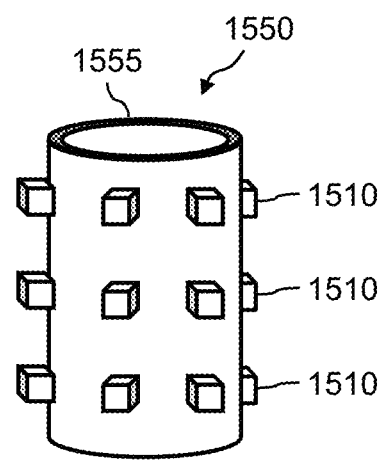
FIG. 15C is another view of the exemplary sensor configuration presented in FIG. 15A, viewed from a side.

Referring now to FIGS. 15A to 15C, an application of the present disclosure is presented according to one exemplary embodiment in system 1500. In some embodiments, a plurality of sensors 1510 may be arranged in a substantially cylindrical array to form, for example a cuff 1550. Cuff 1550 may be sized to fit, for example, around a portion of a patient's body, for example, a patient's arm 1560. In some embodiments, cuff 1550 may be positioned about, for example, the location where a patient is or was injected with a radiopharmaceutical or the like. In some embodiments, cuff 1550 may include a deformable transition layer 1555 that may be utilized to maintain a consistent or otherwise known material composition and/or density between a radioactive source 1503 and the sensors 1510, such as for example, to substantially eliminate air gaps. In some embodiments, the transition layer 1555 may include water, saline, and/or various other gels or materials. In some embodiments, the materials may be substantially similar in density to human tissue and/or bone.

In some embodiments, the sensors 1510 of cuff 1550 may also be arranged to provide for substantially "stacked" sensors at various locations on cuff 1550. For example, and similar to the exemplary cubic configuration discussed above with reference to FIG. 14, the plurality of sensors 1510 may be arranged to have a first, inner substantially cylindrical configuration and a second, outer substantially cylindrical configuration, thereby providing for two or more sensors 1510 proximate a plurality of desired locations, with one of the sensors 1510 being relatively farther away from the source 1503 than another sensor 1510.

In the event of an infiltration, for example, the system 1500 could be used according to some or all of the methods taught hereinabove to estimate the magnitude, location, and/or volume of the infiltrated radioactive material in the patient. Advantageously, the system may also be utilized, in some embodiments, to provide estimates of the magnitude, location, and volume over time, thereby providing critical information to healthcare providers regarding, among many other things, the rate at which radioactive material is being introduced into the bloodstream and therefore affecting, for example, nuclear imaging, and to quantify the patient's tissue exposure to the infiltrated radiation at or around the injection site, to name just a few.

Figure 16:
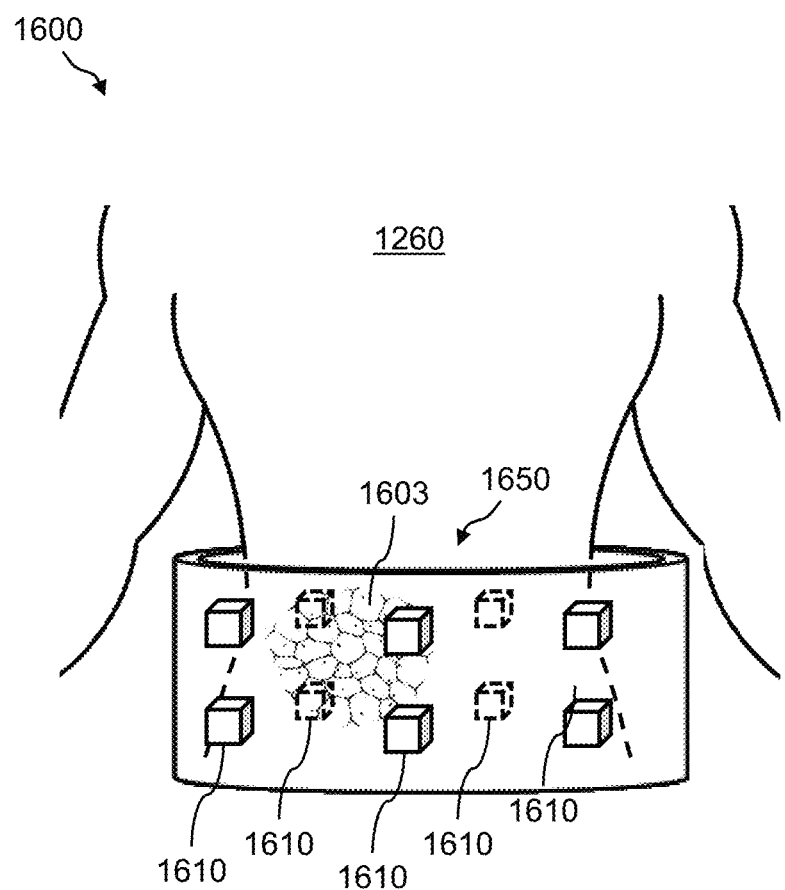
FIG. 16 is an exemplary sensor configuration according to some embodiments of the present disclosure.

In certain other embodiments, similar arrangements of sensors may be utilized in other configurations for use in other areas of the body. For example, referring now to FIG. 16, a larger cuff-like configuration 1650 may be utilized to surround the torso or pelvic region of a patient 1260, for example. Such arrangements may enable users to estimate, for example, radiopharmaceutical uptake in a tumor or organ (i.e. organ dosimetry) in the body. As presented above, any arrangement of sensors may be used, and therefore other configurations of sensors may be utilized as needed to fit the nature of the area to be measured. For example, a horseshoe figuration, a flexible sheet configuration, or any other.

Figure 17:
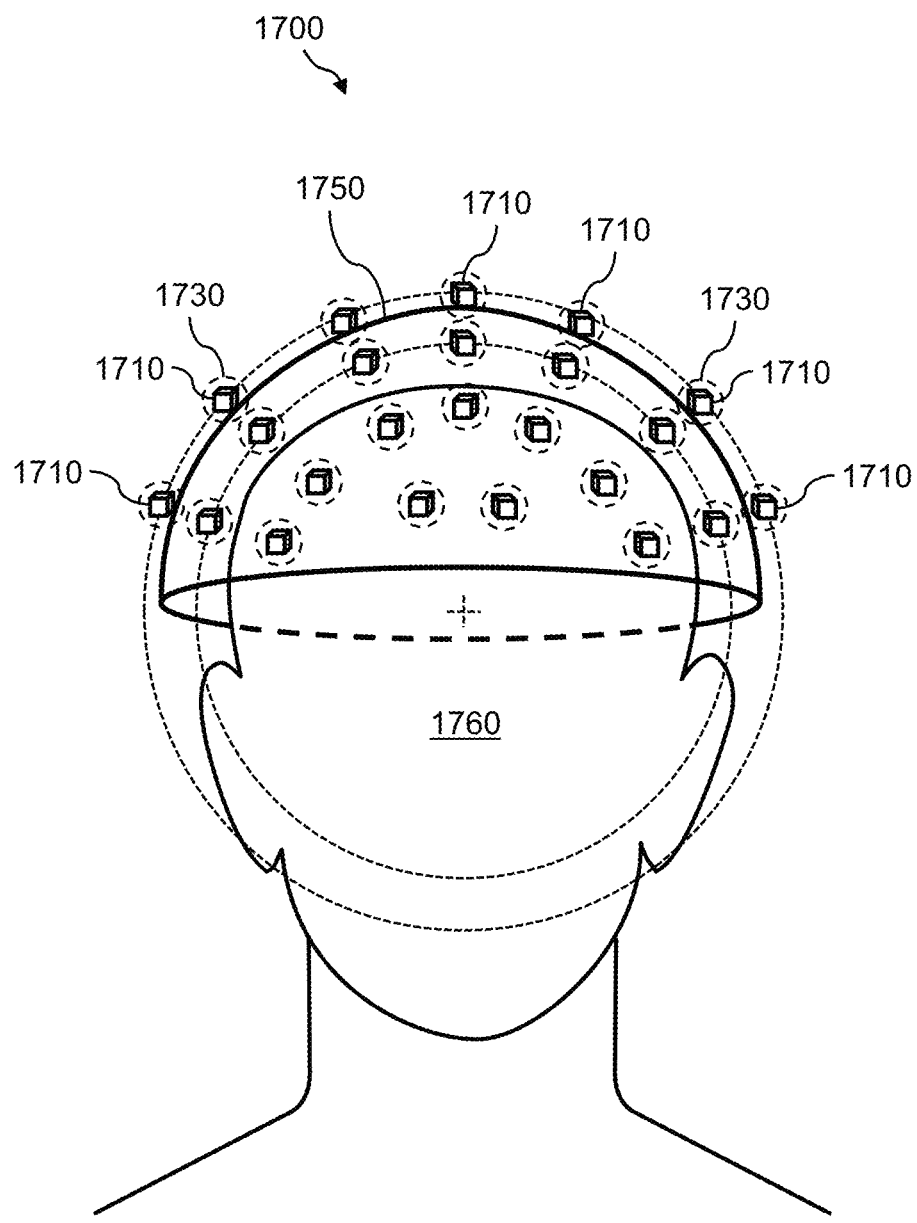
FIG. 17 is an exemplary sensor configuration according to some embodiments of the present disclosure.

Referring now to FIG. 17, yet another exemplary configuration of a system 1700 of the present disclosure is presented. In some embodiments, it may be desirable to estimate the uptake of radioactive material in all or a portion(s) of the brain. According to some embodiments, then, a plurality of sensors 1710 may be arranged in a helmet-like article 1750 such that the sensors 1710 may be arranged about a patient's head 1760. The sensors 1710 may be arranged in any manner about the helmet 1750, including in those several configurations discussed herein. In the exemplary embodiment illustrated in FIG. 17, the sensors 1710 may be disposed about the helmet 1750 in a generally hemispherical configuration and may in some embodiments also include two sensors 1710 at each measurement location 1730. In some embodiments, helmet 1750 may include a first set of sensors 1710 disposed in a first hemispherical configuration, and a second set of sensors 1710 disposed in a second hemispherical configuration, with the second hemispherical configuration having a slightly larger radius than the first. Accordingly, in some embodiments, there may be two (or more) sensors 1710 about a plurality of desired locations 1730 where one sensor 1710 at each location 1730 is slightly farther away from source 1703 than a second sensor 1710.

The helmet 1750 may also include a transition layer similar to layer 1555 in FIG. 15 comprising material(s) of known composition and/or density (e.g., water, saline, or gel(s) having a density and other properties similar to that of brain tissue, other tissue, bone (e.g., skull), etc., as desired), thereby eliminating air gaps that could, in some circumstances, complicate the estimations and/or introduce undesirable error.

In each of these various embodiments, the relative distance between sensors may initially be unknown given the need to modify the cuff 1550, 1650 or helmet 1750 to fit the various sizes and shapes of patients presented. To calibrate the various systems 1500, 1600, and/or 1700 (and others) before use, the systems and methods taught herein may be modified to introduce known radioactive elements at known locations. For example, relatively small doses of cesium, for example, may be introduced at a known location, from which the relative locations of each sensor may be determined by the system.

In another example, known amounts of cesium (or some other radioactive material) may be introduced to determine the specific density of a patient's body through which the particles released from a radiopharmaceutical may travel.

By determining reliable estimates of one or more of the magnitude, location, and/or volume of a radioactive source material in the body, it may be possible to, among many other things, evaluate treatment efficacy, make clinical decisions or diagnoses, identify or eliminate medical conditions, compare different areas of the body (e.g., different hemispheres of the bran) and make clinical decisions and/or diagnoses based on such measurements and/or by comparing such measurements to past measurements of the patient and/or measurements of the general population, among many other things. The systems and methods taught herein are expected not only to provide such estimates, but to use such estimates to aid clinicians in their diagnosis and treatment, and even suggest or determine appropriate clinical decisions and/or diagnosis.

The invention may be embodied in other specific forms without departing from the spirit or essential characteristics thereof. The present embodiments are therefore to be considered in all respects as illustrative and not restrictive, the scope of the invention being indicated by the claims of the application rather than by the foregoing description, and all changes which come within the meaning and range of equivalency of the claims are therefore intended to be embraced therein.

What is claimed is:

1. A method for the ex vivo real-time detection over a period of time of radiation emitted by a subject from the administration of a radioactive analyte that decays in vivo, the method comprising:
   (i) positioning an array of ex vivo radiation measurement sensors proximate to a point of administration on the subject of the radioactive analyte, wherein the array has a known geometry and relative distances between the sensors are known;
   (ii) detecting radiation over a desired period of time and producing signal data associated with the desired period of time, wherein the measurement sensors each have at least one sensor output for such signal data, and outputting the signal data;

(iii) processing the signal data using a computer processor in operative communication with a non-transient memory and the measurement sensor outputs by performing the steps of:
   (a) receiving the signal data associated with the desired period of time;
   (b) using a measured value of radioactive material proximate the point of administration at a time t, estimating a function of radioactive material proximate the point of administration from a time of administration to the time t based only on the signal data associated with the desired period of time;
   (c) determining, based on the estimated function of radioactive material proximate the point of administration, a radioactivity, location, and volume of radioactive material disposed in body tissue proximate the point of injection from the time of administration to the time t.

2. The method of claim 1, further comprising the step of amplifying the signal data using a signal amplifier in operable communication with the radiation sensors.

3. The method of claim 1, further comprising the step of estimating a dose of radiation to an area of affected tissue.

4. A system for the ex vivo real-time detection over a period of time of radiation emitted by a subject from the administration of a radioactive analyte that decays in vivo, the system comprising:
   at least one ex vivo radiation measurement sensor to detect radiation over a desired period of time and to produce signal data associated with the desired period of time, the ex vivo measurement sensor adapted to sensing radiation proximate to a point of administration on the subject of the radioactive analyte;
   a signal amplifier in operable communication with the radiation measurement sensor, the signal amplifier adapted to amplify the signal data, the radiation measurement sensor having at least one sensor output for such amplified signal data;
   at least one computer processor and a non-transient memory, the computer processor in operable communication with the non-transient memory and the measurement sensor output;
   wherein the non-transient memory includes computer program code executable by the at least one computer processor, the computer program code configured for performing the steps of receiving the amplified signal data with the desired period of time, accessing a measured amount of radioactive material proximate the point of administration at a time t, and using the amplified signal data alone, estimating a function of radioactive material proximate the point of injection as a function of time from a time of injection to time t;
   wherein the measured value of radioactive material proximate the point of administration at time t is measured using an array of two or more ex vivo radiation measurement sensors, wherein the array has a known geometry and relative distances between the sensors are known such that a distance from the array to a radiometric center of the radioactive material being measured can be determined, and further wherein a radioactivity, location, and volume of the radioactive material being measured can be determined.

5. The system of claim 4, further comprising the step of convolving the estimated function with a known impulse response from a typical bolus injection using the computer processor, and calculating a correction factor to be applied to one or more measurements made using a nuclear imaging device.

6. A method for the ex vivo real-time determination over a period of time of the radioactivity, location, and volume of a radioactive source in the body by measuring radiation that decays in vivo emitted by a subject, the method comprising:
   (i) applying one or more ex vivo radiation measurement sensors proximate an area of interest on a patient;
   (ii) detecting radiation over a desired period of time and producing signal data associated with the desired period of time;
   (iii) amplifying the signal data using a signal amplifier in operable communication with the radiation measurement sensor, wherein the radiation measurement sensor has at least one sensor output for such amplified signal data, and outputting the amplified signal data;
   (iv) processing the amplified signal data using a computer processor in operative communication with a non-transient memory and the measurement sensor output by performing the steps of:
      (a) receiving the amplified signal data associated with the desired period of time;
      (b) comparing the amplified signal data to a set of expected signal data for radioactive sources of various radioactivities, locations, and volumes;
      (c) determining a radioactivity, location, and volume of the radioactive source in the body over the desired period of time by fitting the amplified signal data to the most likely set of expected signal data.

7. The method of claim 6, wherein a Maximum Likelihood Expectation Maximization method is used to fit the most likely radioactivity, location, and volume of the radioactive source in the body.

8. The method of claim 6, further comprising the step of determining a dose of radioactivity to an area of tissue proximate the location of the radioactive source.

9. The method of claim 6, further comprising the step of using the determined radioactivity, location, and volume of radioactive source in the body to make one or more of a clinical decision or diagnosis.

10. The method of claim 6, wherein an array comprising two or more of the ex vivo radiation measurement sensors is utilized.

11. The method of claim 10, wherein the array of two or more sensors are disposed in a substantially symmetric geometry about the radioactive source in the body.

12. The method of claim 10, wherein the two or more radiation measurement sensors are disposed proximate one or more desired measurement locations, and further wherein each desired measurement location comprises at least a first sensor disposed relatively closer to the radioactive source than a second sensor.

13. The method of claim 6, wherein radioactivity, location, and volume are determined for two or more radiation sources in the body.

14. The method of claim 13, further comprising the step of comparing the determined radioactivity, location, or volume of the two or more radioactive sources, and making a clinical decision or diagnosis based on the comparison.

15. The method of claim 14, wherein the clinical decision or diagnosis is also based on one or more prior determinations or comparisons of the subject patient.

16. The method of claim 14, wherein the clinical decision or diagnosis is further based on a comparison to a table comprising data from a population of other patients.

* * * * *